United States Patent
Comellas Freymond et al.

(10) Patent No.: US 10,328,114 B2
(45) Date of Patent: Jun. 25, 2019

(54) LUNG INJURY REPAIR COMPOSITIONS AND METHODS

(71) Applicant: University of Iowa Research Foundation, Iowa City, IA (US)

(72) Inventors: Alejandro P. Comellas Freymond, Iowa City, IA (US); Xiaopeng Li, Iowa City, IA (US); Joseph Zabner, Iowa City, IA (US); Luis Guillermo Vargas Buonfiglio, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/925,826

(22) Filed: Oct. 28, 2015

(65) Prior Publication Data

US 2016/0120934 A1    May 5, 2016

Related U.S. Application Data

(60) Provisional application No. 62/069,694, filed on Oct. 28, 2015.

(51) Int. Cl.
*A61K 38/10* (2006.01)
*A61K 38/00* (2006.01)
*A61K 38/17* (2006.01)

(52) U.S. Cl.
CPC ............ *A61K 38/10* (2013.01); *A61K 38/005* (2013.01); *A61K 38/1709* (2013.01)

(58) Field of Classification Search
CPC ... A61K 38/1709; A61K 38/10; A61K 38/005
See application file for complete search history.

(56) References Cited

U.S. PATENT DOCUMENTS

| | | | |
|---|---|---|---|
| 4,938,949 | A | 7/1990 | Borch et al. |
| 6,855,549 | B1 | 2/2005 | McCray, Jr. et al. |
| 7,585,865 | B2 | 9/2009 | Antonetti et al. |
| 2012/0190611 | A1* | 7/2012 | Braiman-Wiksman ............... A61K 38/10 514/1.7 |

OTHER PUBLICATIONS

By Arimori et al., Antiviral Research, 2013, 99, 230-237.*
MedlinePlus Medical Encyclopedia, Interstitial lung disease, Jul. 28, 2016.*
Levitt, et al., "Treatment of acute lung injury: historical perspective and potential future therapies", Semin Respir Crit Care Med 27(4), 426-437 (2006).
Li, et al., "Integrin α6β4 identifies human distal lung epithelial progenitor cells with potential as a cell-based therapy for cystic fibrosis lung disease", PLoS One 8(12), e83624 (2013).
Llado, et al., "Repression of Intestinal Stem Cell Function and Tumorigenesis through Direct Phosphorylation of β-Catenin and Yap by PKCζ", Cell Rep 10, 740-754 (2015).
Luzina, et al., "PKCalpha mediates CCL18-stimulated collagen production in pulmonary fibroblasts", Am J Respir cell Mol Biol 35, 298-305 (2006).
Matthay, et al., "The acute respiratory distress syndrome", J Clin Invest 122(8), 2731-2740 (2012).
Matute-Bello, et al., "Animal models of acute lung injury", Am J Physiol Lung Cell Mol Physiol 295(3), L379-399 (2008).
Mondrinos, et al., "Protein kinase C and acute respiratory distress syndrome", Shock 39(6), 467-479 (2013).
Mouratis, et al., "Modeling pulmonary fibrosis with bleomycin", Curr Opin Pulm Med 17(5), 355-361 (2011).
Namati, et al., "In vivo micro-CT lung imaging via a computer-controlled intermittent iso-pressure breath hold (IIBH) technique", Phys Med Biol 51(23), 6061-6075 (2006).
Ohta, et al., "Altered expression of tight junction molecules in alveolar septa in lung injury and fibrosis", Am J Physiol Lung Cell Mol Physiol 302(2), L193-205 (2012).
Paul, et al., "Dynamic changes in intracellular ROS levels regulate airway basal stem cell homeostasis through Nrf2-dependent Notch signaling", Cell Stem Cell 14, 199-214 (2014).
Pickrell, et al., "Lung connective tissue measurements. I. Amino acid analysis procedures for determination of canine lung connective tissue", Archives of Internal Medicine 127, 891-895 (1971).
Pittet, et al., "TGF-beta is a critical mediator of acute lung injury", J Clin Invest 107(12), 1537-1544 (2001).
Rajendran, et al., "Inhibition of protein kinase C signaling maintains rat embryonic stem cell pluripotency", J Biol Chem 288(34), 24351-24362 (2013).
Schultz-Cherry, et al., "Influenza virus neuraminidase activates latent transforming growth factor beta", J Virol 70(12), 8624-8629 (1996).
Short, et al., "Pathogenesis of influenza-induced acute respiratory distress syndrome", Lancet Infect Dis 14(1), 57-69 (2014).
Short, et al., "Protein kinase Czeta attenuates hypoxia-induced proliferation of fibroblasts by regulating MAP kinase phosphatase-1 expression", Molecular Biology of the Cell 17, 1995-2008 (2006).
Sinn, et al., "Viscoelastic gel formulations enhance airway epithelial gene transfer with viral vectors", Am J Respir Cell Mol Biol 32 (5), 404-410 (2005).
Sjoqvist, et al., "PKCζ regulates Notch receptor routing and activity in a Notch signaling-dependent manner", Cell Research 24, 433-450 (2014).
Stevenson, "Understanding tight junction clinical physiology at the molecular level", J Clin Invest 104(1), 3-4 (1999).
Strengert, et al., "Analysis of epithelial barrier integrity in polarized lung epithelial cells", Methods Mol Biol 763, 195-206 (2011).

(Continued)

*Primary Examiner* — Rachael E Bredefeld
*Assistant Examiner* — Kaipeen E Yang
(74) *Attorney, Agent, or Firm* — Viksnins Harris Padys Malen LLP

(57) ABSTRACT

The present invention provides a pharmaceutical composition comprising Protein Kinase C Zeta (PKC-ζ) inhibitor and therapeutic methods for preventing or treating a pathological condition or symptom or for inducing proliferation of lung progenitor cells in a mammal by administering the PKC-ζ inhibitor.

6 Claims, 7 Drawing Sheets
Specification includes a Sequence Listing.

(56) References Cited

OTHER PUBLICATIONS

Stuart, et al., "Regulated assembly of tight junctions by protein kinase C", Proc Natl Acad Sci 92(13), 6072-6076 (1995).
Suzuki, et al., "aPKC kinase activity is required for the asymmetric differentiation of the premature junctional complex during epithelial cell polarization", J Cell Sci 115(Pt18), 3565-3573 (2002).
Thompson, et al., "Epidemiology of seasonal influenza: use of surveillance data and statistical models to estimate the burden of disease", J Infect Dis 194 Suppl 2, S82-S91 (2006).
Tsukita, et al., "Multifunctional strands in tight junctions", Nat Rev Mol Cell Biol. 2(4), 285-293 (2001).
Turner, et al., "'Putting the squeeze' on the tight junction: understanding cytoskeletal regulation", Semin Cell Dev Biol 11(4), 301-308 (2000).
Vaughan, et al., "Regenerative activity of the lung after epithelial injury", Biochim Biophys Acta 1832(7), 922-930 (2013).
Walkey, et al., "Acute respiratory distress syndrome: epidemiology and management approaches", Clin Epidemiol 4, 159-169 (2012).
Wallach-Dayan, et al., "Bleomycin initiates apoptosis of lung epithelial cells by ROS but not by Fas/FasL pathway", Am J Physiol Lung Cell Mol Physiol 290(4), L790-L796 (2006).
Wang, et al., "Heterogeneity of claudin expression by alveolar epithelial cells", Am J Respir Cell Mol Biol 29(1), 62-70 (2003).
Wansleeben, et al., "Age-related changes in the cellular composition and epithelial organization of the mouse trachea", PLoS One 9, e93496 (2014).
Ware, et al., "The acute respiratory distress syndrome", N Engl J Med 342(18), 1334-1349 (2000).
Yao, et al., "Protein kinase C zeta mediates cigarette smoke/aldehyde- and lipopolysaccharide-induced lung inflammation and histone modifications", J Biol Chem 285(8), 5405-5416 (2010).
Zheng, et al., "Evidence for Scgb1a1(+) cells in the generation of p63(+) cells in the damaged lung parenchyma", Am J Respir Cell Mol Biol 50(3), 595-604 (2014).
Zuo, et al., "p63(+)Krt5(+) distal airway stem cells are essential for lung regeneration", Nature 517, 616-620 (2015).
Bagegni, et al., "Inhibition of PKC-ζ Activation Prevents Bleomycin Induced Lung Injury and Promotes Lung Repair", ACCP Meeting, Abstract, Chest 144:466A (Oct. 2013).
Bagegni, et al., "PKC-ζ Activation is Required for Bleomycin Induce Lung Injury", ATS International Conference, Abstract, Am J Respir Crit Care Med, 187, A1229 (2013).
Balda, et al., "The ZO-1-associated Y-box factor ZONAB regulates epithelial cell proliferation and cell density", J Cell Biol 160(3), 423-432 (2003).
Barkauskas, et al., "Type 2 alveolar cells are stem cells in adult lung", J Clin Invest 123, 3025-3036 (2013).
Bautista, et al., "Clinical aspects of pandemic 2009 influenza A (H1N1) virus infection", N Engl J Med 362(18), 1708-1719 (2010).
Blank, et al., "Epidemiology of ARDS and ALI", Crit Care Clin 27(3), 439-458 (2011).
Borcherding, et al., "The Role of PKC-ζ in Lung Fibrosis", D38 Cellular and Molecular Regulation of Lung Fibrosis, Thematic Poster Session, Pennsylvania Convention Center, May 22, 2013.
Breitkreutz, et al., "Protein kinase C family: on the crossroads of cell signaling in skin and tumor epithelium", J Cancer Res Clin Oncol 133(11), 793-808 (2007).
Brower, et al., "Ventilation with lower tidal volumes as compared with traditional tidal volumes for acute lung injury and the acute respiratory distress syndrome. The Acute Respiratory Distress Syndrome Network", New Engl Journal of Med 342, 1301-1308 (2000).
Budinger, et al., "Active transforming growth factor-beta1 activates the procollagen I promoter in patients with acute lung injury", Intensive Care Medicine 31, 121-128 (2005).
Buonfiglio, et al., "Protein Kinase Cζ Inhibitor Promotes Resolution of Bleomycin-Induced Acute Lung Injury", Am J Respir Cell Mol Biol, 1-9 (2016).
Burnham, et al., "Detection of fibroproliferation by chest high-resolution CT scan in resolving ARDS", Chest 146(5), 1196-1204 (2014).
Bush, et al., "Genesis and reversal of the ischemic phenotype in epithelial cells", J Clin Invest 106(5), 621-626 (2000).
Caraballo, et al., "Ambient particulate matter affects occludin distribution and increases alveolar transepithelial electrical conductance", Respirology 16(2), 340-349 (2011).
Caraballo, et al., "Hypoxia increases transepithelial electrical conductance and reduces occludin at the plasma membrane in alveolar epithelial cells via PKC-ζ and PP2A pathway", Am J Physiol Lung Cell Mol Physiol 300, L569-L578 (2011).
Caraballo, et al., "Protein Kinase C-ζ Mediates Lung Injury Induced by Diesel Exhaust Particles", Am J Respir Cell Mol Biol, vol. 48 (3), 306-313 (2013).
Chapman, et al., "Integrin α6β4 identifies an adult distal lung epithelial population with regenerative potential in mice", J Clin Invest 121(7), 2855-2862 (2011).
Chen, et al., "Airway epithelial progenitors are region specific and show differential responses to bleomycin-induced lung injury", Stem Cells 30, 1948-1960 (2012).
Chesnutt, et al., "Early detection of type III procollagen peptide in acute lung injury. Pathogenetic and prognostic significance", Am Journal of Respiratory and Critical Care Medicine 156, 840-845 (1997).
Chiba, et al., "Transmembrane proteins of tight junctions", Biochim Biophys Acta 1778(3), 588-600 (2008).
Clarke, et al., "Protein kinase C activation leads to dephosphorylation of occludin and tight junction permeability increase in LLC-PK1 epithelial cell sheets", J Cell Sci 113 (Pt 18), 3187-3196 (2000).
Curley, et al., "Cell therapy demonstrates promise for acute respiratory distress syndrome—but which cell is best?", Stem Cell Res Ther 4(2), 29 (2013).
Dada, et al., "Hypoxia-induced endocytosis of Na,K-ATPase in alveolar epithelial cells is mediated by mitochondrial reactive oxygen species and PKC-zeta", J Clin Invest 111(7), 1057-1064 (2003).
Dempsey, et al., "Protein kinase C isozymes and the regulation of diverse cell responses", Am J Physiol Lung Cell Mol Physiol 279(3), L429-438 (2000).
Dodane, et al., "Identification of isoforms of G proteins and PKC that colocalize with tight junctions", J Membr Biol 149(3), 199-209 (1996).
Duran, et al., "Crosstalk between PKCzeta and the IL4/Stat6 pathway during T-cell-mediated hepatitis", EMBO J 23(23), 4595-4605 (2004).
Duran, et al., "Essential role of RelA Ser311 phosphorylation by zetaPKC in NF-kappaB transcriptional activation", EMBO J 22(15), 3910-3918 (2003).
Eichholtz, "A myristoylated pseudosubstrate peptide, a novel protein kinase C inhibitor", J Biol Chem 268(3), 1982-1986 (1993).
Englert, et al., "A role for the receptor for advanced glycation end products in idiopathic pulmonary fibrosis", Am J Pathol 172(3), 583-591 (2008).
Fahy, et al., "The acute respiratory distress syndrome: a role for transforming growth factor-beta 1", Am J Respir Cell Mol Biol 28, 499-503 (2003).
Gjyshi, et al., "Kaposi's sarcoma-associated herpesvirus induces Nrf2 activation in latently infected endothelial cells through SQSTM1 phosphorylation and interaction with polyubiquitinated Keap1", Journal of Virology 89, 2268-2286 (2015).
Gobran, et al., "PKC isoforms and other signaling proteins involved in surfactant secretion in developing rat type II cells", Am J Physiol 274 (6 Pt 1), L901-7, (1998).
Golebiewski, et al., "The avian influenza virus NS1 ESEV PDZ binding motif associates with Dlg1 and Scribble to disrupt cellular tight junctions", J Virol 85(20), 10639-10648 (2011).
Gonzalez-Mariscal, et al., "Tight junction proteins", Prog Biophys Mol Biol 81(1), 1-44 (2003).
Goss, et al., "Incidence of acute lung injury in the United States", Critical Care Medicine 31(6), 1607-1611 (2003).

(56) References Cited

OTHER PUBLICATIONS

Gotts, et al., "Influenza causes prolonged disruption of the alveolar-capillary barrier in mice unresponsive to mesenchymal stem cell therapy", Am J Physiol Lung Cell Mol Physiol 307(5), L395-406 (2014).

He, et al., "Mitochondrial Cu,Zn-superoxide dismutase mediates pulmonary fibrosis by augmenting H2O2 generation", J. Biol. Chem. 286, 15597-15607 (2011).

Hofmann, "The potential for isoenzyme-selective modulation of protein kinase C", FASEB J 11(8), 649-669 (1997).

Hogan, et al., "Repair and regeneration of the respiratory system: complexity, plasticity, and mechanisms of lung stem cell function", Cell Stem Cell 15, 123-138 (2014).

Khalil, et al., "Regulation of the effects of TGF-beta 1 by activation of latent TGF-beta 1 and differential expression of TGF-beta receptors (T beta R-I and T beta R-II) in idiopathic pulmonary fibrosis", Thorax 56, 907-915 (2001).

Khalil, et al., "TGF-beta 1, but not TGF-beta 2 or TGF-beta 3, is differentially present in epithelial cells of advanced pulmonary fibrosis: an immunohistochemical study", Am J Respir Cell Mol biol 14, 131-138 (1996).

Konishi, et al., "Activation of protein kinase C by tyrosine phosphorylation in response to H2O2", Proc Natl Acad Sci 94(21), 11233-11237 (1997).

Kotton, et al., "Lung regeneration: mechanisms, applications and emerging stem cell populations", Nature Medicine 20, 822-832 (2014).

Kumar, et al., "Distal airway stem cells yield alveoli in vitro and during lung regeneration following H1N1 influenza infection", Cell 147(3), 525-538 (2011).

Kunzelmann, et al., "Influenza virus inhibits amiloride-sensitive Na+ channels in respiratory epithelia", Proc Natl Acad Sci 97(18), 10282-10287 (2000).

Lafemina, et al., "Claudin-18 deficiency results in alveolar barrier dysfunction and impaired alveologenesis in mice", Am J Respir Cell Mol Biol 51(4), 550-558 (2014).

Lafemina, et al., "Keratinocyte growth factor enhances barrier function without altering claudin expression in primary alveolar epithelial cells", Am J Physiol Lung Cell Mol Physiol 299(6), L724-734 (2010).

Lawson, et al., "Increased and prolonged pulmonary fibrosis in surfactant protein C-deficient mice following intratracheal bleomycin", Am J Pathol 167(5), 1267-1277 (2005).

Lazrak, et al., "Influenza virus M2 protein inhibits epithelial sodium channels by increasing reactive oxygen species", FASEB J 23(11), 3829-3842 (2009).

Leitges, et al., "Targeted disruption of the zetaPKC gene results in the impairment of the NF-kappaB pathway", Mol Cell 8(4), 771-780 (2001).

* cited by examiner

LUNG INJURY REPAIR COMPOSITIONS AND METHODS

RELATED APPLICATION

The present patent application claims benefit of U.S. Application Ser. No. 62/069,694 filed on Oct. 28, 2014, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Nov. 12, 2015, is named 17023_156US1_SL.txt and is 846 bytes in size.

BACKGROUND OF THE INVENTION

Acute lung injury (ALI) is a fatal complication of influenza infections. In particular, the elderly is a population at risk of increase morbidity and mortality from influenza infection. A critical mediator of ALI is transforming growth factor beta (TGF-β), which can be activated directly by influenza virus. ALI is characterized by three phases: i) In the exudative phase there is an increase in alveolar-capillary permeability, increase inflammatory markers in the bronchoalveolar lavage fluid (BALF) and impairment of lung compliance. Impairment of the alveolar epithelial barrier by disruption of cell adhesion proteins is an important mechanism during this phase. ii) In the fibroproliferative phase there is increase collagen deposition and lung fibrosis. iii) In the resolution phase, proliferation and differentiation of lung progenitor cells play a role in lung repair mechanisms.

ALI includes Acute Respiratory Distress Syndrome (ARDS) and also milder forms of lung injury. ARDS is a sudden failure of the respiratory system, characterized by widespread inflammation of the lung that leads to fluid leaking into the alveoli, impairing gas exchange. It is associated with pulmonary cytokine release, impaired endothelial barriers, fluid accumulation in distal airspaces, and fibrotic changes. ARDS is a clinical syndrome characterized by hypoxemia, bilateral lung infiltrates, and normal wedge pressure. Approximately 250,000 Americans develop ALI annually (Goss, Christopher H., et al. "Incidence of acute lung injury in the United States." *Critical care medicine* 31.6 (2003): 1607-1611). Approximately 190,000 Americans develop ARDS annually (http://www.lung.org/lung-disease/acute-respiratory-distress-syndrome/understanding-ards.html). An estimated 132,000 people in the US have pulmonary fibrosis, with many more having some form of interstitial lung disease. All of these diseases harm lung tissue.

The primary causes of ARDS/ALI are sepsis (infection of the bloodstream), inhalation of harmful substances, severe pneumonia, and viral infections that affect the lungs (influenza, MERS, SARS, Ebola, Hunta Virus, etc.). The only current treatment of ARDS/ALI is lung protective ventilation. Despite recent improvements in ventilation strategies, ARDS mortality continues to be close to 40%. If ventilation is not successful, a lung transplant is necessary. There are currently no medications that repair lung tissue. Therefore, there is a critical need to develop novel and effective therapies for patients with ALI, and especially in patients with influenza induced ALI.

SUMMARY OF THE INVENTION

In certain embodiments, the present invention provides a pharmaceutical composition comprising a peptide of SEQ ID NO:1 (Ser-Ile-Tyr-Arg-Arg-Gly-Ala-Arg-Arg-Trp-Arg-Lys-Leu-OH) or SEQ ID NO:2 (N-Myristoyl-Ser-Ile-Tyr-Arg-Arg-Gly-Ala-Arg-Arg-Trp-Arg-Lys-Leu-OH) and a physiologically acceptable carrier.

In certain embodiments, the present invention provides a therapeutic method for preventing or treating a pathological condition or symptom in a mammal, such as a human, wherein lung cell injury is implicated and cellular repair is desired, comprising administering to a mammal in need of such therapy, an effective amount of a composition comprising a peptide of SEQ ID NO:1 (Ser-Ile-Tyr-Arg-Arg-Gly-Ala-Arg-Arg-Trp-Arg-Lys-Leu-OH) or SEQ ID NO:2 (N-Myristoyl-Ser-Ile-Tyr-Arg-Arg-Gly-Ala-Arg-Arg-Trp-Arg-Lys-Leu-OH) and a physiologically acceptable carrier. In certain embodiments, the pathological condition is Acute Respiratory Distress Syndrome, Interstitial Lung Disease, Acute Lung Injury, or Pulmonary Fibrosis.

In certain embodiments, the present invention provides a therapeutic method for inducing proliferation of lung progenitor cells in a mammal, such as a human, wherein lung progenitor cell proliferation is desired, comprising administering to a mammal in need of such therapy, an effective amount of a composition comprising a peptide of SEQ ID NO:1 (Ser-Ile-Tyr-Arg-Arg-Gly-Ala-Arg-Arg-Trp-Arg-Lys-Leu-OH) or SEQ ID NO:2 (N-Myristoyl-Ser-Ile-Tyr-Arg-Arg-Gly-Ala-Arg-Arg-Trp-Arg-Lys-Leu-OH) and a physiologically acceptable carrier. In certain embodiments, the peptide is administered intravenously, orally, by inhalation, by dry powder, by bronchoscopic instillation, or by intra-airway (tracheal or bronchial) aerosol. In certain embodiments, the disease is ALI. In certain embodiments, the subject is a mammal, such as a human. In certain embodiments the disease symptoms are reduced by at least 1%, 5%, 10%, 20, 30%, 40%, 50%, 60%, 70%, 80%, 90% 95%, or 99%.

In certain embodiments, the peptide is administered multiple times, such as at daily intervals, every 48 hours, every 72 hours, or weekly.

In certain embodiments, cell proliferation is increased by at least 10% as compared the mammal prior to treatment.

In certain embodiments, the present invention provides a method to treat lung cell injury or to induce proliferation of lung progenitor cells comprising administering a therapeutically effective amount of a composition comprising a peptide of SEQ ID NO:1 (Ser-Ile-Tyr-Arg-Arg-Gly-Ala-Arg-Arg-Trp-Arg-Lys-Leu-OH) or SEQ ID NO:2 (N-Myristoyl-Ser-Ile-Tyr-Arg-Arg-Gly-Ala-Arg-Arg-Trp-Arg-Lys-Leu-OH) and a physiologically acceptable carrier. In certain embodiments, the cell proliferation level is increased by at least about 10%, 20, 30%, 40%, 50%, 60%, 70%, 80%, 90% 95%, or 99%. In certain embodiments, the cell is a lung cell, a nasal cell, a tracheal cell, a bronchial cell, a bronchiolar or alveolar epithelial cell.

In certain embodiments, the present invention provides a composition comprising a peptide of SEQ ID NO:1 (Ser-Ile-Tyr-Arg-Arg-Gly-Ala-Arg-Arg-Trp-Arg-Lys-Leu-OH) or SEQ ID NO:2 (N-Myristoyl-Ser-Ile-Tyr-Arg-Arg-Gly-Ala-Arg-Arg-Trp-Arg-Lys-Leu-OH) and a physiologically acceptable carrier for use in medical therapy.

received initial instillation of Bleomycin+DMSO (first arrow in "Bleo" and "Bleo/PKC" scheme) followed by PBS+DMSO. iii) Bleomycin/PKCζi (Bleo/PKCζi): received initial instillation of Bleomycin+DMSO, followed by PBS+PKCζi (all arrows except the first one in the "Bleo/PKC" scheme). Mice were euthanized at week 1, 3 and 6. (B) Densitometry of Western Blot of mouse lungs treated with Bleo/PKCζi showed decreased p-PKCζ at week 1 compared to Bleo group. (C) Immunostaining of p-PKCζ showed decreased intensity in the Bleo/PKCζi group compared to bleomycin group at week 3 and 6. (Scale bar=10 μm).

Figure 2:
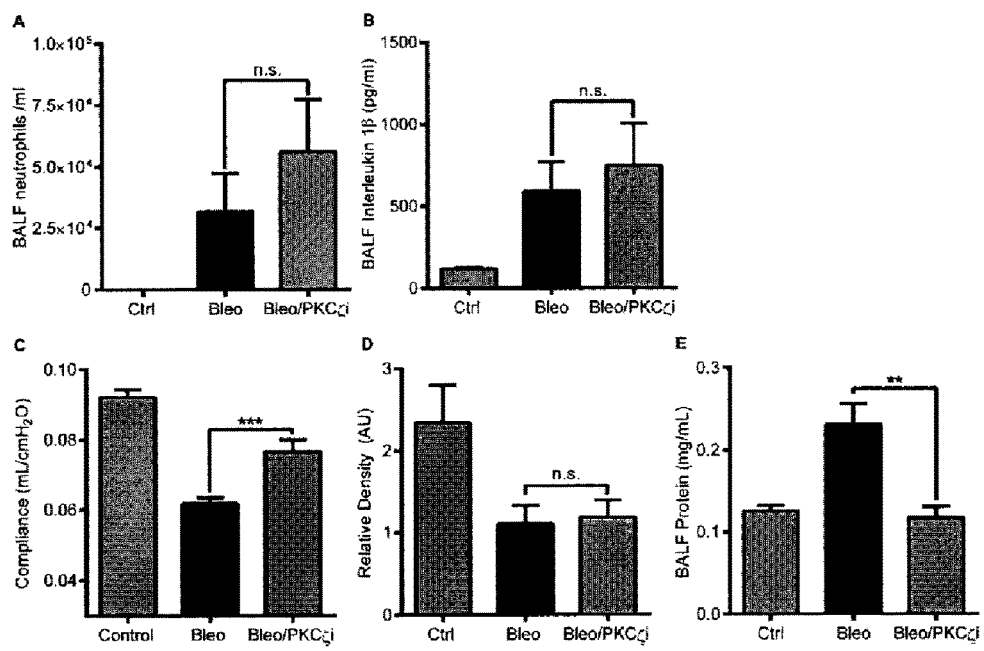

FIG. 2. PKCζ does not prevent bleomycin-induced lung inflammation but preserves lung compliance and decreased lung protein permeability. BALF in mice was collected at week 1 post injury. (A) PKCζi does not decrease bleomycin induced increase in the BALF neutrophil concentration. (B) PKCζi does not decrease IL-1β release into BALF. (C) Lung compliance was assessed in mice at week 1 post injury. PKCζi preserves lung compliance compare to bleomycin. (D) PKCζi does not prevent total SPC decrease in the lungs. (E) PKCζi prevents increase in BALF protein concentration in bleomycin treated mice. All results are expressed as mean±SE (p<0.01, * p<0.001).

Figure 3:
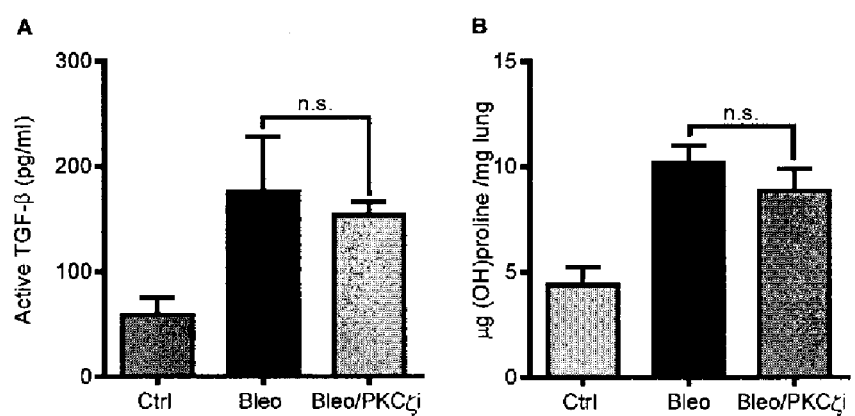

FIG. 3. PKCζi does not prevent increase in TGF β activation and collagen deposition in the lungs. Mice lung were harvested at week 3 post injury. (A) PKCζi does not prevent bleomycin induced TGF β activation. (B) PKCζi does not decrease hydroxyproline concentration.

Figure 4:
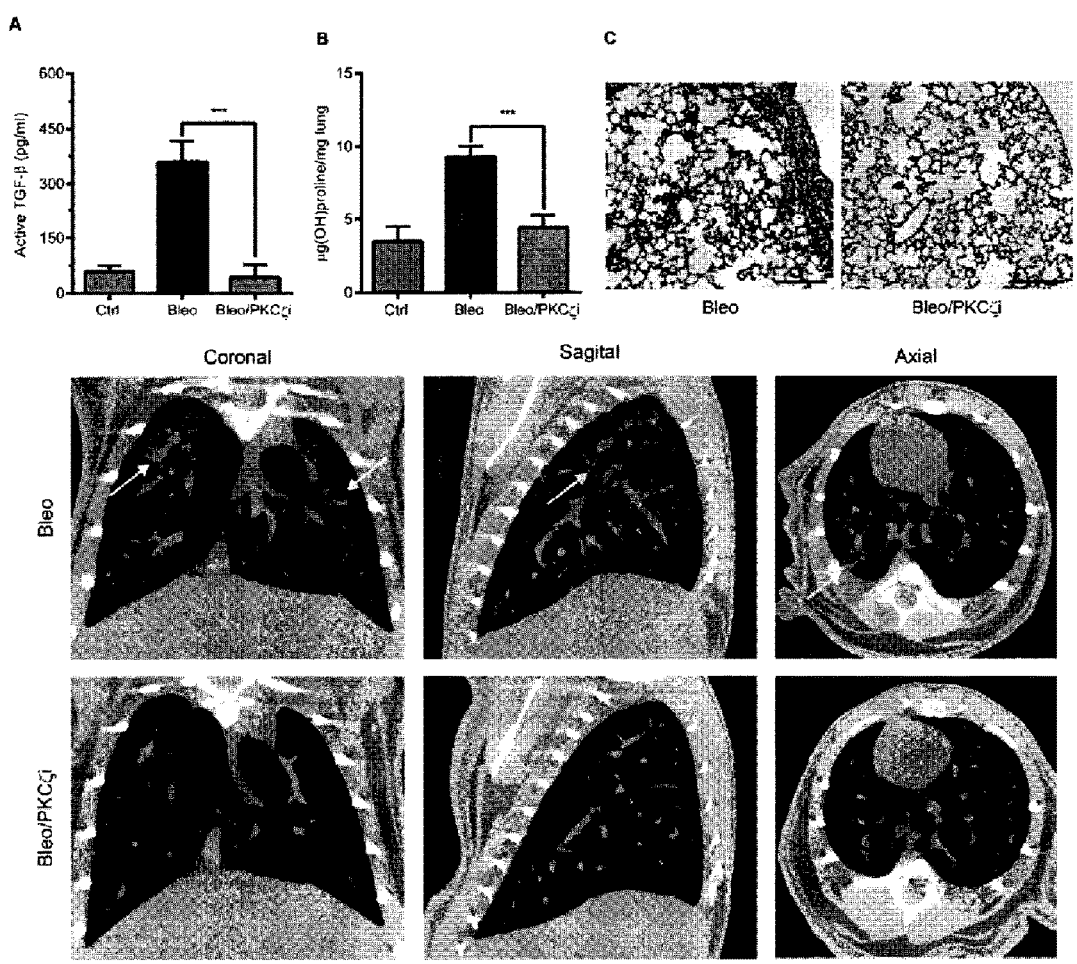

FIG. 4. PKCζi promotes lung repair in vivo. Mice were followed up to 6 weeks, underwent in vivo μCT scans and lungs harvested to measure hydroxyproline concentration and to perform masson's staining. (A) PKCζi prevents bleomycin induced active TGF β at week 6. (B) PKCζi treated mice have decreased hydroxyproline concentration at week 6 compare to bleomycin group. (C) PKCζi treated mice have decreased collagen lung deposition by masson's staining at week 3 compared to bleomycin group. (Scale bar=50 μm). (D) Representative cross-sectional μCT at week 6 of the cohort captured (Bleomycin n=3 and PKCζ n=3). Lungs showed evidence of lung injury (arrows) in the bleomycin group and complete resolution in the PKCζi group at week 6. All results are expressed as mean±SE (*** p<0.001).

Figure 5:
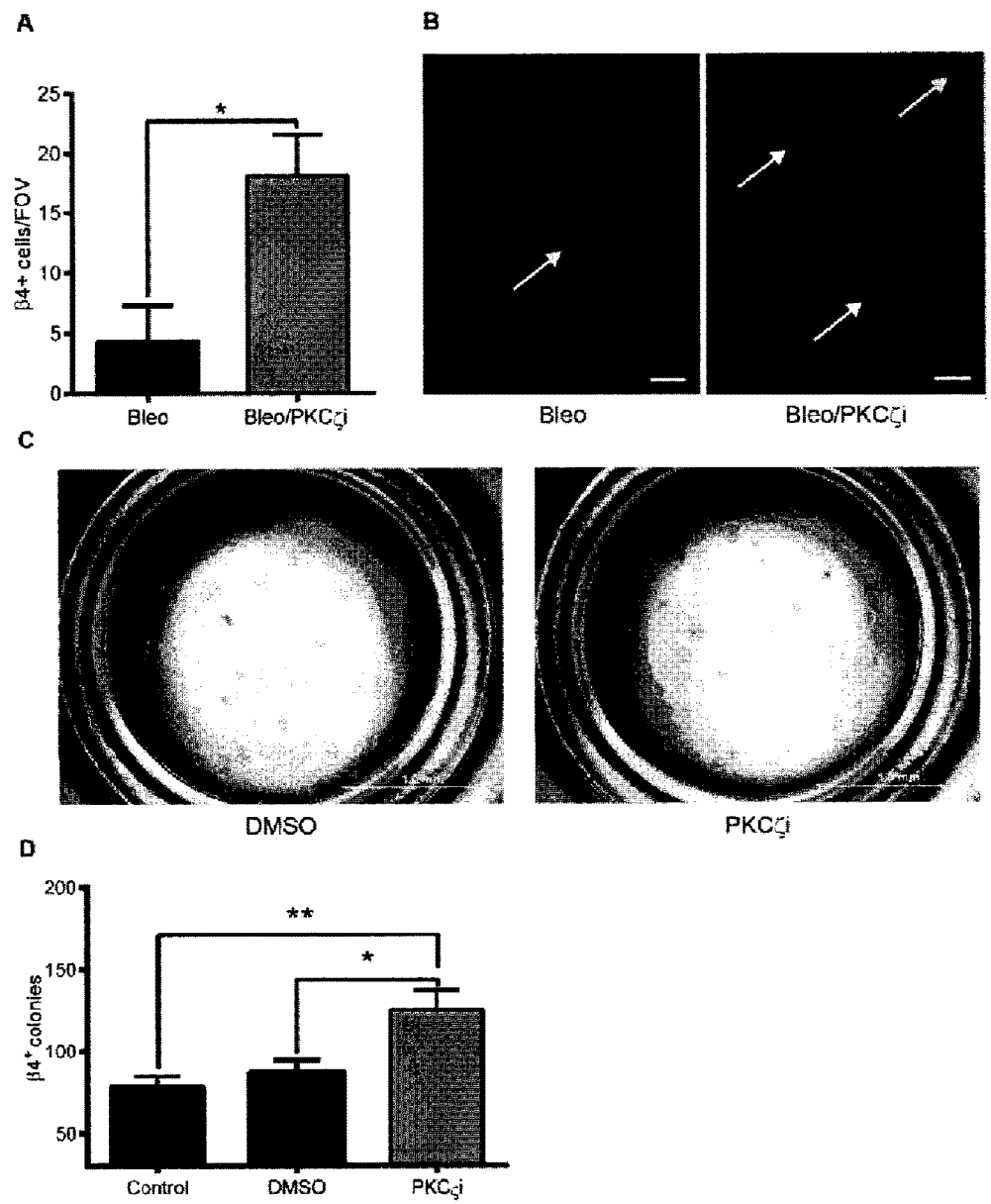

FIG. 5. PKCζi promotes proliferation of DLEP integrin β4+ cells in vivo and in vitro. Mice lungs were harvested at week 3 and 6 post injury. (A) PKCζi treated mice have an increased number of lung DLEP integrin β4+ cells compared to bleomycin group at week 6. (B) Representative immunofluorescence image of increased number of β4+ cells (arrows) at week 6 in the Bleo/PKCζi group. (Scale bar=20 μm). (C) Representative images of 2× macroscopic view of β4+ derived colonies in matrigel in the DMSO and PKC-ζi group at week 2. (B) Isolated β4+ cells supplemented with 20% BALF from bleomycin injured mice media were treated with PBS, DMSO or PKCζi for two weeks. PKC-ζi increased the number of β4+ colonies compared to PBS and DMSO at week 2 (n=6 in two different experiments). All the results are expressed as mean±SE (* p<0.05).

Figure 6:
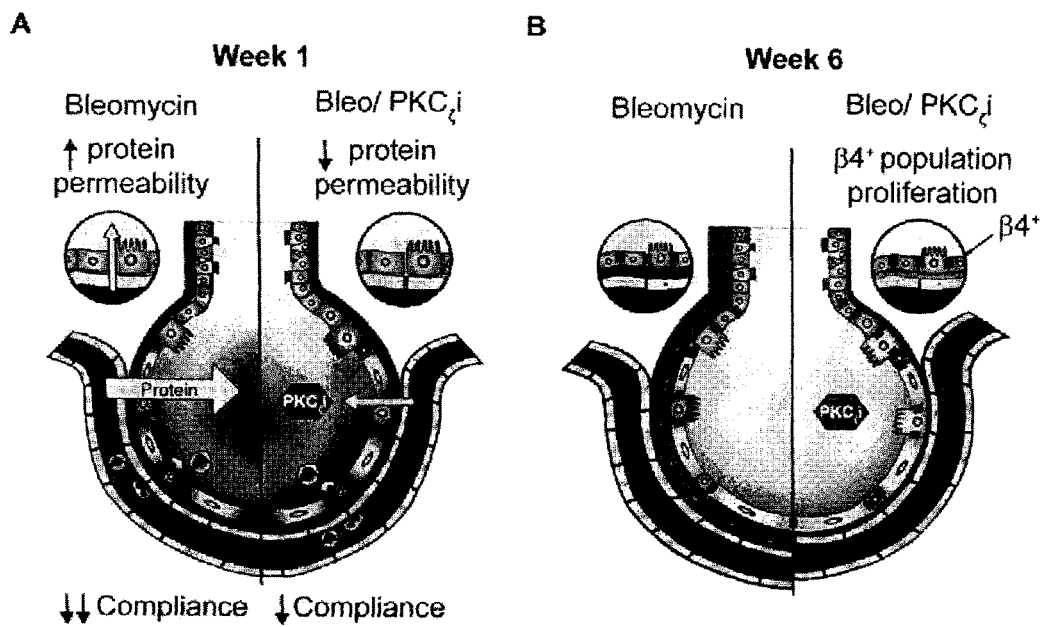

FIG. 6. Suggested PKCζi mechanism in ALI resolution. The suggested role of PKCζi in ALI is: (A) Exudative Phase, characterized by impaired lung compliance and increase in: alveolar-capillary permeability, neutrophil infiltration and inflammatory markers in the BALF. PKCζi is suggested to decrease protein permeability and increase lung compliance. (B) Resolution Phase, characterized by proliferation and differentiation of lung progenitor cells that play a role in lung repair mechanisms. PKCζi is suggested to promote integrin β4+ DLEP cell proliferation.

Figure 7:
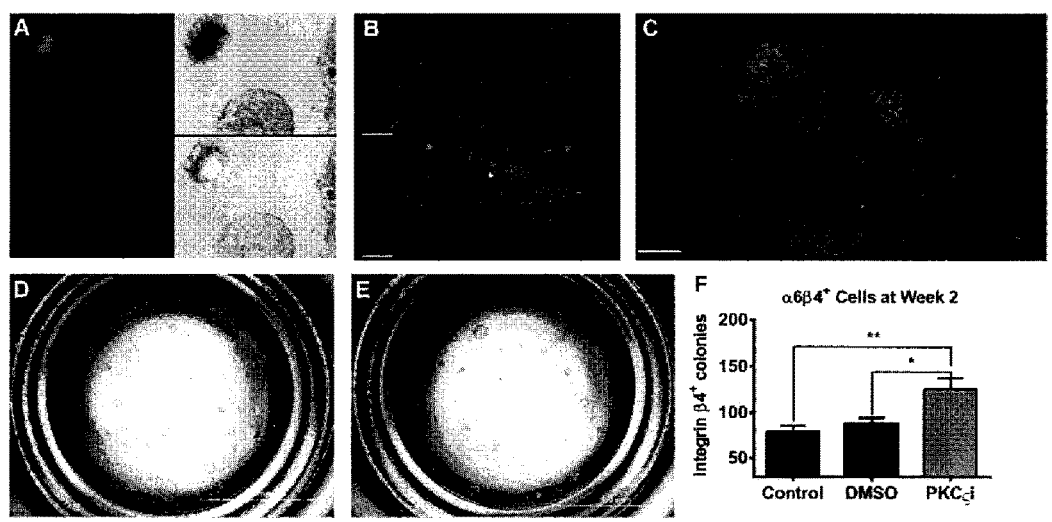

FIG. 7. PKCζi promotes proliferation DLEP α6β4+ cells in vitro. (A) A6β4+ colonies can differentiate into SPC+ cells. Composite of GFP, Tomato red, DIC, and merged. Tomato red is ubiquitous and green is SPC. (Scale bar 100 μm). (B) Cross section of a α6β4+ colony in matrigel forming a 3D organoid. Nucleus stained with Hoechst (blue) (C) Upper view of the colonies (B&C; Scale bar 50 μm). (D&E) 2× view of DMSO (D) and PKCζi (E) wells at week 2. (F) Quantification of DLEP α6β4+ colonies at week 2 (n=6). Results are expressed as mean±SE (* p<0.05, **p<0.01).

DETAILED DESCRIPTION

Epithelial tissues, such as those in the lung, provide a physical barrier between biologic compartments and against bacteria and other pathogens, but they also mediate vectorial and selective transport of ions, water and macromolecules. The establishment and maintenance of selectively permeable barriers is determined by proteins such as E-cadherin in the adherens junction, and the occludin/claudin families in the tight junctions (Bush et al., (2000). "Genesis and reversal of the ischemic phenotype in epithelial cells." *J Clin Invest* 106(5): 621-626). The latter are sites of cell-cell contact composed of a number of transmembrane and peripheral proteins, assembled into a complex tethered to the cytoskeleton (Turner, J. R. (2000). "'Putting the squeeze' on the tight junction: understanding cytoskeletal regulation." *Semin Cell Dev Biol* 11(4): 301-308). Tight junctions have been implicated in multiple cellular functions, including modulation of inflammation, cell migration, ion movement, development, cell proliferation and cell polarity (Balda et al., (2003). "The ZO-1-associated Y-box factor ZONAB regulates epithelial cell proliferation and cell density." *J Cell Biol* 160(3): 423-432). The transmembrane integral proteins comprising tight junctions (i.e., occludin, claudins and junctional adhesion molecules) are linked to the cytoskeleton through interactions with cytoplasmic peripheral proteins, including the zonula occludens (ZO-1, ZO-2, and ZO-3). It has been reported that keratinocyte growth factor (KGF) enhances barrier function of AEC without altering any of the tight junction (TJ) proteins, by modulating the actin cytoskeleton (Tsukita et al. (2001). "Multifunctional strands in tight junctions." *Nat Rev Mol Cell Biol* 2(4): 285-293) and actin binding proteins; Stevenson, B. R. (1999). "Understanding tight junction clinical physiology at the molecular level." *J Clin Invest* 104(1): 3-4; LaFemina et al. (2010). "Keratinocyte growth factor enhances barrier function without altering claudin expression in primary alveolar epithelial cells." *Am J Physiol Lung Cell Mol Physiol* 299(6): L724-734). This result demonstrates that there are multiple targets to improve the alveolar epithelial barrier, but that the mechanisms involved in the dysfunction and disruption of the alveolar epithelial barrier are not well understood. Alveolar type II (ATII) cells in culture have transepithelial electrical resistance (TER) of >500 Ω·cm2, or its reciprocal transepithelial electrical conductance (Gt) of 1-2 mS/cm2, which is consistent with the formation of tight junctions (Wang, et al., (2003). "Heterogeneity of claudin expression by alveolar epithelial cells." *Am J Respir Cell Mol Biol* 29(1): 62-70). Accordingly, ATII cells express all of the components of tight junctions including occludin, ZO-1 and different claudins (3, 4, 5 and 18) (Wang, et al., (2003). "Heterogeneity of claudin expression by alveolar epithelial cells." *Am J Respir Cell Mol Biol* 29(1): 62-70). Also, our laboratory reported that hypoxia and ambient particulate matter disrupt alveolar epithelial tight junctions via ROS production and activation of PKCζ (Caraballo, et al. (2013). "Protein kinase C-zeta mediates lung injury induced by diesel exhaust particles." *Am J Respir Cell Mol Biol* 48(3): 306-313; Caraballo, et al. (2011). "Hypoxia increases transepithelial electrical conductance and reduces occludin at the plasma membrane in alveolar epithelial cells via PKC-zeta and PP2A pathway." *Am J Physiol Lung Cell Mol Physiol* 300(4): L569-578; Caraballo, et al. (2011). "Ambient particulate matter affects occludin distribution and increases alveolar transepithelial electrical conductance." *Respirology* 16(2): 340-349). Recently, Ohta et al (Ohta, et al. (2012). "Altered expression of tight junction molecules in alveolar septa in lung injury and fibrosis." *Am J Physiol Lung Cell Mol Physiol* 302(2): L193-205) demonstrated in an experimental bleomycin-induced lung injury model that transforming growth factor beta (TGF-β), a critical mediator of ALI and that in part reduces lung epithelial cells TER (Pittet, et al. (2001). "TGF-beta is a critical mediator of acute lung injury." *J Clin Invest* 107(12): 1537-1544), was responsible for reducing the expression of claudin-5 and 18. Furthermore, claudin-18 has been recognized as an important tight junction protein that maintains the alveolar epithelial barrier integrity and plays a role in alveologenesis (LaFemina, et al. (2014). "Claudin-18 deficiency results in alveolar barrier dysfunction and impaired alveologenesis in mice." Am J Respir Cell Mol Biol.).

Protein Kinases C are serine-threonine kinases that have several regulating roles including inflammation (Duran, et al. (2003). "Essential role of RelA Ser311 phosphorylation by zetaPKC in NF-kappaB transcriptional activation." *Embo J* 22(15): 3910-3918; Duran, et al. (2004). "Crosstalk between PKCzeta and the IL4/Stat6 pathway during T-cell-mediated hepatitis." *Embo J* 23(23): 4595-4605; Yao et al. (2010). "Protein kinase C zeta mediates cigarette smoke/aldehyde- and lipopolysaccharide-induced lung inflammation and histone modifications." *J Biol Chem* 285(8): 5405-5416), cell polarity (Suzuki, et al. (2002). "aPKC kinase activity is required for the asymmetric differentiation of the premature junctional complex during epithelial cell polarization." *J Cell Sci* 115(Pt 18): 3565-3573) and regulates assembly of tight junctions (Stuart, et al. (1995). "Regulated assembly of tight junctions by protein kinase C." *Proc Natl Acad Sci USA* 92(13): 6072-6076) and occluding phosphorylation (Dodane, et al. (1996). "Identification of isoforms of G proteins and PKCζ that colocalize with tight junctions." *J Membr Biol* 149(3): 199-209). Mondrinos et al. recently reviewed the mechanism of PKC isoforms in the pathogenesis of ALI and potential therapeutic interventions by selectively inhibiting or activating specific PKCζ isoforms (Mondrinos, et al. (2013). "Protein kinase C and acute respiratory distress syndrome." *Shock* 39(6): 467-479). One of this isoform is PKC-ζ that belongs to the family of atypical PKC, characterized for its activation being independent of calcium or diacylglycerol (Breitkreutz, et al. (2007). "Protein kinase C family: On the crossroads of cell signaling in skin and tumor epithelium." *J Cancer Res Clin Oncol* 133(11): 793-808). PKC-ζ is express in the lung (Leitges, et al. (2001). "Targeted disruption of the zetaPKC gene results in the impairment of the NF-kappaB pathway." *Mol Cell* 8(4): 771-780), and activated by reactive oxygen species (ROS) in AECs (Dada, et al. (2003). "Hypoxia-induced endocytosis of Na,K-ATPase in alveolar epithelial cells is mediated by mitochondrial reactive oxygen species and PKC-zeta." *J Clin Invest* 111(7): 1057-1064). A recent report demonstrated that PKC-inhibition maintains rat embryonic stem cell pluripotency (Rajendran, et al. (2013). "Inhibition of protein kinase C signaling maintains rat embryonic stem cell pluripotency." *J Biol Chem* 288(34): 24351-24362). Most TJ integral proteins require that scaffolding proteins mediate an association with the actin cytoskeleton—the exception being occludin, which interacts directly with F-actin via a 150 amino acid C-terminal domain. This domain also directly binds to ZO-1, another protein that binds to the actin cytoskeleton (Chiba, et al. (2007). "Transmembrane proteins of tight junctions." *Biochim Biophys Acta*), and mediates occludin self-association. Among species, these terminal 150 amino acids of occludin are remarkably well-conserved, and likely form a typical a helical coiled-coil structure. This region also associates with the regulatory kinase PKC-ζ (Gonzalez-Mariscal, et al. (2003). "Tight junction proteins." *Prog Biophys Mol Biol* 81(1): 1-44). This is particularly interesting as it has been reported that PKCs could be upstream in the signaling pathway regulating epithelial barrier function; and, in fact, PKCs can regulate the kinases and phosphatases that target occludin (Clarke, et al. (2000). "Protein kinase C activation leads to dephosphorylation of occludin and tight junction permeability increase in LLC-PK1 epithelial cell sheets." *J Cell Sci* 113 (Pt 18): 3187-3196). Our laboratory has reported that a PKC-ζ inhibitor preserves the alveolar epithelial barrier in a model of hypoxia and diesel exhaust particle induced ALI by preserving occludin at the plasma membrane (Caraballo, et al. (2011). "Hypoxia increases transepithelial electrical conductance and reduces occludin at the plasma membrane in alveolar epithelial cells via PKC-zeta and PP2A pathway." *Am J Physiol Lung Cell Mol Physiol* 300(4): L569-578; Caraballo, et al. (2011). "Ambient particulate matter affects occludin distribution and increases alveolar transepithelial electrical conductance." *Respirology* 16(2): 340-349).

In the development of ALI, the mechanisms of lung repair are fundamental for the recovery of patients. For example, mesenchymal stem/stromal cells (MSCs) are multipotent, self-renewing cells that secrete anti-inflammatory cytokines and epithelial and endothelial growth factors which in different mouse lung injury models have shown to promote lung repair (Curley, et al. (2013). "Cell therapy demonstrates promise for acute respiratory distress syndrome—but which cell is best?" *Stem Cell Res Ther* 4(2): 29). However, Gotts et al. tested this therapeutic intervention in an influenza ALI mouse model showing that this therapy was ineffective in promoting lung repair (Gotts, et al. (2014). "Influenza causes prolonged disruption of the alveolar-capillary barrier in mice unresponsive to mesenchymal stem cell therapy." *Am J Physiol Lung Cell Mol Physiol*.), concluding that influenza induced ALI have different mechanisms of injury and repair. One potential difference between ALI due to influenza infection and other scenarios of ALI is that in the former the initial insult occurs in the epithelium, while the latter occurs in the endothelium (Short, et al. (2014). "Pathogenesis of influenza-induced acute respiratory distress syndrome." *Lancet Infect Dis* 14(1): 57-69).

Lung epithelial progenitor cells that play an important role in lung repair include Clara cells and Alveolar type II cells. More recently, Chapman et al. reported that integrin α6β4 identifies an adult distal lung epithelial population with regenerative potential in mice, which can maintain type II AEC during lung repair (Chapman, et al. (2011). "Integrin alpha6beta4 identifies an adult distal lung epithelial population with regenerative potential in mice." *J Clin Invest* 121(7): 2855-2862). Furthermore, Li et al. reported that this same integrin α6β4 identifies human distal lung epithelial progenitor cells (Li, et al. (2013). "Integrin alpha6beta4 identifies human distal lung epithelial progenitor cells with potential as a cell-based therapy for cystic fibrosis lung disease." *PLoS One* 8(12): e83624). Moreover, in an ALI mouse model induced by H1N1 influenza viral infection, Kumar et al. identified that epithelial "pods" containing Krt5+/Trp63+ basal-like cells after viral infection appear both around the bronchioles and within the alveoli in the areas of greatest damage (Kumar, et al. (2011). "Distal airway stem cells yield alveoli in vitro and during lung regeneration following H1N1 influenza infection." *Cell* 147 (3): 525-538; Wansleeben, et al. (2014). "Age-related changes in the cellular composition and epithelial organization of the mouse trachea." *PLoS One* 9(3): e93496). Krt5+ pods have been identified in mouse lungs after bleomycin injury (Zheng et al. (2014). "Evidence for Scgb1a1(+) cells in the generation of p63(+) cells in the damaged lung parenchyma." *Am J Respir Cell Mol Biol* 50(3): 595-604). What is the origin of those cells is a hot topic in lung injury and repair field. We have shown that α6β4+ human distal lung progenitor cells have the potential to differentiate into K5+ positive cells de novo (Li, et al. (2013). "Integrin alpha6beta4 identifies human distal lung epithelial progenitor cells with potential as a cell-based therapy for cystic fibrosis lung disease." *PLoS One* 8(12): e83624). Chapman et al. have shown that mouse α6β4+ progenitor cells bear the K5+ marker in a mouse H1N1 influenza infection model (unpublished data). Therefore, targeted therapies to α6β4+ epithelial progenitor cells that promote lung repair by regenerating lung epithelial cells have a significant therapeutic potential in patients with ALI.

Viral pneumonias are a common cause of ALI, being influenza virus one of the most common viruses responsible for ALI. The pathogenesis of ALI induced by influenza virus is centered on the alveolar epithelium (Short, et al. (2014). "Pathogenesis of influenza-induced acute respiratory distress syndrome." *Lancet Infect Dis* 14(1): 57-69). Influenza virus recognizes and binds to sialosaccharides on the alveolar epithelial cell surface using viral hemagglutinins and neuroaminidases. Influenza infections share some physiological and biological effects present in other causes of ALI including increase inflammatory lung response, impairment of the alveolar-capillary barrier, and decrease lung compliance. Influenza viral infection increases lung epithelial barrier permeability (Strengert, et al. (2011). "Analysis of epithelial barrier integrity in polarized lung epithelial cells." *Methods Mol Biol* 763: 195-206) and disrupts lung epithelial tight junctions (Golebiewski, et al. (2011). "The avian influenza virus NS1 ESEV PDZ binding motif associates with Dlg1 and Scribble to disrupt cellular tight junctions." *J Virol* 85(20): 10639-10648). In addition, influenza infection, via viral hemagglutinin and increase reactive oxygen species (ROS) production, activates PKCζ (Kunzelmann, et al. (2000). "Influenza virus inhibits amiloride-sensitive Na+ channels in respiratory epithelia." *Proc Natl Acad Sci USA* 97(18): 10282-10287; Chen, et al. (2004). "Influenza virus inhibits ENaC and lung fluid clearance." *Am J Physiol Lung Cell Mol Physiol* 287(2): L366-373.; Lazrak, et al. (2009). "Influenza virus M2 protein inhibits epithelial sodium channels by increasing reactive oxygen species." *FASEB J* 23(11): 3829-3842). Furthermore, viral neuroaminidase can activate TGF-β, an essential mediator in ALI (Schultz-Cherry, et al. (1996). "Influenza virus neuraminidase activates latent transforming growth factor beta." *J Virol* 70(12): 8624-8629; Pittet et al. (2001). "TGF-beta is a critical mediator of acute lung injury." *J Clin Invest* 107(12): 1537-1544).

Pulmonary fibrosis is a respiratory disease caused by excess fibrosis connective tissue in the lungs. This excess connective tissue leads to thickening of the walls of the lung, causing reduced oxygen supply in the blood. It is a common secondary effect of interstellar lung disease. Current treatments for pulmonary fibrosis aim at preventing the spread of the disease. There are no treatments available that rebuild lung tissue. If the disease is severe, a lung transplant may be needed.

Peptides of the Present Invention and Pharmaceutical Compositions

Protein kinases regulate a number of cellular functions. Protein kinase C (PKC) belongs to a group that is expressed in several tissues. Specifically, PKC zeta (PKC-ζ) is abundantly expressed in human lungs and when active it regulates cytoskeleton function, cell adhesion proteins, cell proliferation, and stem cell pluripotency. In addition, TGF-β and influenza virus can activate PKC, including PKC-ζ. PKC-ζ is an enzyme in humans that is very abundant in alveolar epithelium. There, it regulates tight junction (TJ) integrity and mediates changes in the localization of TJ proteins. It has been shown in previous studies that diesel exhaust particulates and hypoxia cause TJ disruption at least in part by PKC-ζ (Dempsey, Edward C., et al. "Protein kinase C isozymes and the regulation of diverse cell responses." *American Journal of Physiology—Lung Cellular and Molecular Physiology* 279.3 (2000): L429-L438; Caraballo, Juan Carlos, et al. "Hypoxia increases transepithelial electrical conductance and reduces occludin at the plasma membrane in alveolar epithelial cells via PKC-ζ and PP2A pathway." *American Journal of Physiology—Lung Cellular and Molecular Physiology* 300.4 (2011): L569-L578).

The present technology relates to the use of Protein Kinase C Zeta inhibitor (PKC-ζi) for the promotion of lung repair for patients suffering from chronic lung diseases such as Acute Respiratory Distress Syndrome, Interstitial Lung Disease, and Pulmonary Fibrosis.

The present invention provides a PKC-ζ inhibitor peptide compound of SEQ ID NO:1 having the following amino acid sequence:

Ser-Ile-Tyr-Arg-Arg-Gly-Ala-Arg-Arg-Trp-Arg-Lys-Leu-OH (SEQ ID NO:1)

Peptide sequences specifically recited herein are written with the amino terminus on the left and the carboxy terminus on the right.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes peptides with reduced peptide bonds, which will prevent proteolytic degradation of the peptide. Also, the term includes the amino acid analog α-amino-isobutyric acid. The term also includes natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene,

*Protecting Groups In Organic Synthesis*; Wiley: New York, 1981, and references cited therein).

In certain embodiments, the peptide is modified by N-terminal myristoylation to form a peptide of SEQ ID NO:2:

N-Myristoyl-Ser-Ile-Tyr-Arg-Arg-Gly-Ala-Arg-Arg-Trp-Arg-Lys-Leu-OH (SEQ ID NO:2)

In certain embodiments, the peptide is a derivative or variant of SEQ ID NO:1 or SEQ ID NO:2, which can be prepared as disclosed in U.S. Pat. Nos. 4,612,302; 4,853,371; and 4,684,620.

By "variant" peptide is intended a peptide derived from the native peptide by deletion (so-called truncation) or addition of one or more amino acids to the N-terminal and/or C-terminal end of the native peptide; deletion or addition of one or more amino acids at one or more sites in the native peptide; or substitution of one or more amino acids at one or more sites in the native peptide. The peptides of the invention may be altered in various ways including amino acid substitutions, deletions, truncations, and insertions. Methods for such manipulations are generally known in the art. For example, amino acid sequence variants of the peptides can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

Pharmaceutical Compositions and Methods of Use

Certain embodiments of the present technology use a PKC-ζ inhibitor peptide to induce proliferation of lung progenitor cells in a patient. This is used clinically to increase the proliferation levels of cells in diseased lungs, thus limiting or preventing the effects of that disease. In certain embodiments, the present invention provides methods of using a therapeutic PKC-ζ inhibitor peptide to treat ALI.

The therapeutic agent is administered to the patient so that the therapeutic agent contacts cells of the patient's respiratory or digestive system. For example, the therapeutic agent may be administered directly via an airway to cells of the patient's respiratory system. The therapeutic agent can be administered intranasally (e.g., nose drops) or by inhalation via the respiratory system, such as by propellant based metered dose inhalers or dry powders inhalation devices.

Formulations suitable for administration include liquid solutions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. The therapeutic agent can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The therapeutic agent, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer. In certain embodiments, administration may be, e.g., aerosol, instillation, intratracheal, intrabronchial or bronchoscopic deposition.

In certain embodiments, the therapeutic agent may be administered in a pharmaceutical composition. Such pharmaceutical compositions may also comprise a pharmaceutically acceptable carrier and other ingredients known in the art. The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices. Viscoelastic gel formulations with, e.g., methylcellulose and/or carboxymethylcellulose may be beneficial (see Sinn et al., *Am J Respir Cell Mol Biol,* 32(5), 404-410 (2005)).

The therapeutic agent can be administered by any conventional method available for use in conjunction with pharmaceuticals, either as individual therapeutic agents or in combination with at least one additional therapeutic agent.

In certain embodiments, the therapeutic agent is administered with an agent that disrupts, e.g., transiently disrupts, tight junctions, such as EGTA (see U.S. Pat. No. 6,855,549).

The total amount of the therapeutic agent administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The therapeutic agent can be formulated as pharmaceutical compositions and administered to a mammalian host, such as a human patient in a variety of forms adapted to the chosen route of administration, i.e., orally, intravenously, or by inhalation.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The therapeutic agent may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the therapeutic agent can be determined by comparing their in vitro activity, and in vivo activity in animal models. Methods for the extrapolation of effective dosages in mice, and other animals, to humans are known to the art; for example, see U.S. Pat. No. 4,938,949.

The amount of the therapeutic agent, or an active salt or derivative thereof, required for use in treatment will vary not only with the particular salt selected but also with the route of administration, the nature of the condition being treated and the age and condition of the patient and will be ultimately at the discretion of the attendant physician or clinician.

Pharmaceutical compositions are administered in an amount, and with a frequency, that is effective to inhibit or alleviate the symptoms of airway epithelial disease (e.g., cystic fibrosis) and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 µM at the airway surface, and may be administered 1 to 3 times per day. It will be apparent that, for any particular subject, specific dosage regimens may be adjusted over time according to the individual need. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful to treat cystic fibrosis. Examples of such agents include antibiotics. Accordingly, in one embodiment the invention also provides a composition comprising a therapeutic agent, or a pharmaceutically acceptable salt thereof, at least one other therapeutic agent, and a pharmaceutically acceptable diluent or carrier. The invention also provides a kit comprising a therapeutic agent, or a pharmaceutically acceptable salt thereof, at least one other therapeutic agent, packaging material, and instructions for administering the therapeutic agent or the pharmaceutically acceptable salt thereof and the other therapeutic agent or agents to an animal to treat cystic fibrosis.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In certain embodiments, the therapeutic agent is directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The present invention also provides a solution that includes a solvent, a polymer dissolved in the solvent and a PKC-ζ inhibitor peptide dispersed in the solvent.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The invention will now be illustrated by the following non-limiting Examples.

Example 1

PKC-ζ Inhibitor Prevents Bleomycin Induced Lung Injury and Promotes Repair

Influenza virus is responsible for the development of acute lung injury (ALI). The recent pandemic of 2009 with the influenza A (H1N1) infection raised worldwide concerns about strategies to prevent and treat influenza infections. Although several research teams have been working on preventive strategies, including vaccination, once a patient develops the infection, the person is at risk of dying due to ALT. In addition, it is recognized that age is a risk factor for developing influenza infections and its complications. During the 2009 pandemic people between 50 and 64 years of age had the highest fatality (Writing Committee of the, W.H.O.C.o.C.A.o.P.I.,E. Bautista et al. (2010). "Clinical aspects of pandemic 2009 influenza A (H1N1) virus infection." *N Engl J Med* 362(18): 1708-1719), while during endemic periods of influenza people 65 years and older have a higher incidence of infections, hospitalizations, and increase mortality (Thompson et al. (2006). "Epidemiology of seasonal influenza: use of surveillance data and statistical models to estimate the burden of disease." *J Infect Dis* 194 Suppl 2: S82-91; Blank et al. (2011). "Epidemiology of ARDS and ALI." *Crit Care Clin* 27(3): 439-458). Except for lung protective ventilation strategies (2000), pharmacological therapies for the treatment of ALI have failed to show a mortality reduction (Levitt et al. (2006). "Treatment of acute lung injury: historical perspective and potential future therapies." *Semin Respir Crit Care Med* 27(4): 426-437).

Acute lung injury (ALI) is characterized by increased reactive oxygen species, increased inflammation, and disruption of the alveolar epithelial barrier. The integrity of the epithelial barrier is dependent on the cell adhesion proteins, especially the tight junctions. Integrity of the alveolar epithelial barrier is important in the development of pulmonary fibrosis. PKC-ζ, an atypical protein kinase, which is abundant in the lung, has been shown to affect alveolar epithelial tight junction integrity. The inventors hypothesized that PKC-ζ is activated in ALI and its inhibition preserves the alveolar epithelial barrier integrity.

To test whether inhibition of PKCζ would prevent the development of acute lung injury the inventors utilized a bleomycin lung injury model, as this is widely used, has low complexity, and it is considered to target the alveolar epithelium (Matute-Bello et al. (2008). "Animal models of acute lung injury." *Am J Physiol Lung Cell Mol Physiol* 295(3): L379-399).

Mice were randomly divided into four groups: (i) control: PBS plus DMSO (1 µl/mouse) (ii) PKC-ζ pseudosubstrate inhibitor (PKC-ζ ps) (1 µg/mouse suspended in DMSO), a pharmacological inhibitor that competes for the pseudosubstrate domain which give specificity to several PKCζ isoforms (Hofmann, J. (1997). "The potential for isoenzyme-selective modulation of protein kinase C." *FASEB J* 11(8): 649-669); (iii) bleomycin: bleomycin suspended in PBS (4 U/kg); and (iv) Bleomycin+PKCζi: bleomycin (4 U/kg) plus (1 µg/mouse) PKCζi. The above conditions were administered intratracheally (50 µL) to 6-8 wk-old mice after 2-5 min of anesthesia with 4% isoflurane via a precision Fortec vaporizer (Cyprane, Keighley, UK). Treatment with DMSO or PKCζi was administered every 72 hours and followed for up to 6 weeks. At 1, 3, and 6 weeks mice were euthanized and lungs harvested. Groups control and PKC-ζi groups were combined as they did not have any significant differences between them.

Results were the following:

(1) PKC-ζi prevented activation of PKC-ζ in vivo. Mouse lungs were harvested at 1, 3, and 6 weeks. Western blot and Immunofluoresce analysis were performed on different conditions. Mice treated with bleomycin had activation of PKC-ζ peaking at 3 weeks. PKC-ζi prevented the activation of PKC-ζ

(2) PKC-ζi did not prevent bleomycin induced inflammation. PKC-ζi did not prevent increase in inflammatory response.

(3) PKC-ζi prevented increase in alveolar-capillary permeability. PKC-ζi BALF protein concentration at one week was similar to control while bleomycin treated mice was increased. In addition, it was examined whether PKC-ζi prevented increase in ROS production. PKC-ζi did not prevent ROS production in bleomycin treated mice, which suggested that PKC-ζi preserves the alveolar-capillary barrier via a mechanism independent of ROS production.

(4) PKC-ζi partially preserves lung compliance. Briefly, trachea was surgically exposed and tracheal cannula (18 gauge, Angiocath, Becton Dickinson, Sandy, Utah, USA) placed and secure in the lumen. The mice were paralyzed using intraperitoneal rocuronium (1 mg/Kg) to prevent spontaneous breathing and mechanically ventilated on a computer controlled respirator (flexiVent, SCIREQ Inc., Montreal, Canada). The ventilator was set up to deliver tidal volume 6 ml/kg for 10 minutes; respiratory rate of 150 breaths/min; 3 $cmH_2O$ positive end expiratory pressure (PEEP). The compliance was determined using the maneuver Pressure-volume ramp volume regulated (PVrV) to calculate the Quasi-static compliance. Mice treated with PKC-ζi had partially preserve lung compliance compared to control. Since lung compliance is the product of an intact epithelial barrier and surfactant production, and PKCζ have been reported to be involved in surfactant production (Gobran et al., (1998). "PKCζ isoforms and other signaling proteins involved in surfactant secretion in developing rat type II cells." *Am J Physiol* 274(6 Pt 1): L901-907), the inventors decided to examine by Western blot analysis total amount of SPC in BALF. PKC-ζi did not prevent a reduction in SPC. Therefore, our results are likely due to preservation of the alveolar epithelial barrier.

(5) PKC-ζi did not prevent the development of the fibroproliferative phase. The fibroproliferative phase is part of the injury-repair process (Burnham et al. (2014). "Detection of Fibroproliferation by Chest High Resolution Computed Tomography in Resolving Acute Respiratory Distress Syndrome." *Chest*). To examine the effect of PKC-ζi on this ALI phase, the inventors harvested mouse lungs after three weeks of bleomycin instillation. PKC-ζi had high concentrations of hydroxyproline and histological evidence of lung collagen deposition, confirming the presence of lung fibrosis. In addition, TGF-β, a key signaling molecule involved in ALI and fibrosis, was significantly elevated in both groups. These results demonstrate that PKC-ζi did not alter the fibroproliferative phase at three weeks.

(6) PKC-ζi promoted lung repair in vivo. Recently, it has been recognized that lung repair mechanisms are essential in the resolution of ALI (Matthay et al., (2012). "The acute respiratory distress syndrome." *J Clin Invest* 122(8): 2731-2740; Vaughan et al., (2013). "Regenerative activity of the lung after epithelial injury." *Biochim Biophys Acta* 1832(7): 922-930). The inventors examined the effect of PKC-ζi treatment at 6 weeks in mice treated with bleomycin. Histological and biochemical evidence showed total resolution of lung fibrosis in the PKC-ζi treated group while it persisted in the bleomycin group. Moreover, lung micro CT of bleomycin and PKC-ζi treated groups confirmed lung injury resolution. This demonstrates that PKC-ζi promoted ALI resolution and repair in vivo.

(7) Treatment of mice with PKC-ζi after initial injury continues to be effective in preserving lung compliance. Since the majority of clinical scenarios involve the treatment of patients with established ALI, we set out to examine the effect of PKC-ζi post injury by instilling 6 and 24 hours after bleomycin instillation. Lung compliance was measured at one week. Instillation of PKC-ζi 6 hours post injury prevented the decrease in lung compliance, whereas treatment 24 hours post injury had no protective effect.

(8) PKC-ζi promotes proliferation of distal lung epithelial progenitor cells. Recently Chapman et al reported that integrin α6β4 identifies a population of lung cells with regenerative potential in mice (Chapman et al. (2011). "Integrin alpha6beta4 identifies an adult distal lung epithelial population with regenerative potential in mice." *J Clin Invest* 121(7): 2855-2862). Furthermore, Li et al, reported same population in human lungs (Li et al. (2013). "Integrin alpha6beta4 identifies human distal lung epithelial progenitor cells with potential as a cell-based therapy for cystic fibrosis lung disease." *PLoS One* 8(12): e83624). Therefore, the inventors set out to examine by immunofluorescence the presence of these cells in mouse lungs at 3 and 6 weeks after bleomycin treatment. At three weeks there was an increase trend in α6β44 in the PKC-ζi treated mice, and this became significant at 6 weeks. In addition, the inventors isolated mouse α6β4 cells and treated them for 2 weeks with PKC-ζi (concentration). PKC-ζi increased the number of α6β4 cells compared to DMSO treated cells. These results show the PKC-ζi increase α6β4 proliferation in vitro and in vivo.

Conclusion

In conclusion, it was found that bleomycin causes acute lung injury and pulmonary fibrosis, and activates PKC-ζ. PKC-ζ inhibitor prevents increased protein content in BAL in bleomycin induced ALI. Also, PKC-ζ plays an important role in the disruption of the alveolar epithelial barrier. The preservation of the barrier is most likely due to adhesions and tight junction integrity. PKC-ζ inhibitor decreases the fibroproliferative phase evident by reduction in hydroxyproline and TGF β, and PKC-ζ inhibitor promotes repair.

Example 2

PKCζ Inhibitor Promotes Lung Repair in a Bleomycin Induced Acute Lung Injury Model Acute lung injury (ALI) has an incidence of 200,000 cases per year in the US (1). Despite recent improvements in ventilation strategies, ALI mortality continues to be close to 40%. Therefore, there is a critical need to develop new therapeutic targets in the treatment of patients with ALI.

Based on Matthay and colleagues, ALI is comprised of three phases: First, during the exudative phase there is evidence of lung inflammation, disruption of the alveolar-capillary barrier, hypoxia and decreased lung compliance. The injurious event concomitantly activates a fibroproliferative phase where inflammatory mediators continue to cause injury and there is increased lung collagen deposition and remodeling. Finally, there is a resolution phase where lung edema is reabsorbed and epithelial repair occurs. In addition, lung progenitor cells proliferation and differentiation seems to play a key role in proper lung repair (2-4).

Protein Kinases C (PKC) are ubiquitous serine-threonine kinases that have several biological roles including cell polarity (5), inflammation (6-8), regulation of the cytoskeleton (9-11), and proliferation of pluripotent stem cells (12, 13). In addition, several PKCs have been implicated in the pathogenesis of ALI (14). One isoform is Protein Kinase C zeta (PKCζ) this belongs to the family of atypical PKC, characterized by its calcium or diacylglycerol independent activation (15). PKCζ is highly expressed in the lung (16) and reactive oxygen species (ROS) activate PKCζ (17).

PKCζ is phophorylated in several in vitro models of lung injury and the use of a myristoylated PKCζ pseudosubstrate inhibitor (PKCζi) prevents the disruption of the epithelial barrier in isolated rat primary alveolar epithelial cells (18, 19). PKCζi binds to the pseudo-substrate sequence and inhibits phosphorylation of the myristoylated alanine-rich C kinase substrate protein, which is specific for each PKCζ isozyme and keeps the enzyme inactive (20).

Multiple reports have demonstrated that PKCζ inhibition increases stem cell proliferation population including rat embryonic stem cells and mouse intestinal stem cells (12, 13) making inhibition of PKCζ a potential therapeutic target to promote lung repair in patients with ALI.

The inventors hypothesized that PKCζi would promote early lung injury resolution. To test these hypotheses in vivo, the alveolar epithelium of mice were injured primarily by intratracheal instillation of bleomycin since this model is technically well standardized, reproducible (21) and considered a good screening model to test novel therapeutics in ALI (22). The effect of PKCζi was measured in several parameters of lung injury and repair. Its effect on the proliferation of the novel distal lung progenitor Integrin β4$^+$ cell in vivo and in vitro was evaluated.

Methods

Bleomycin Lung Injury Model

Figure 1:
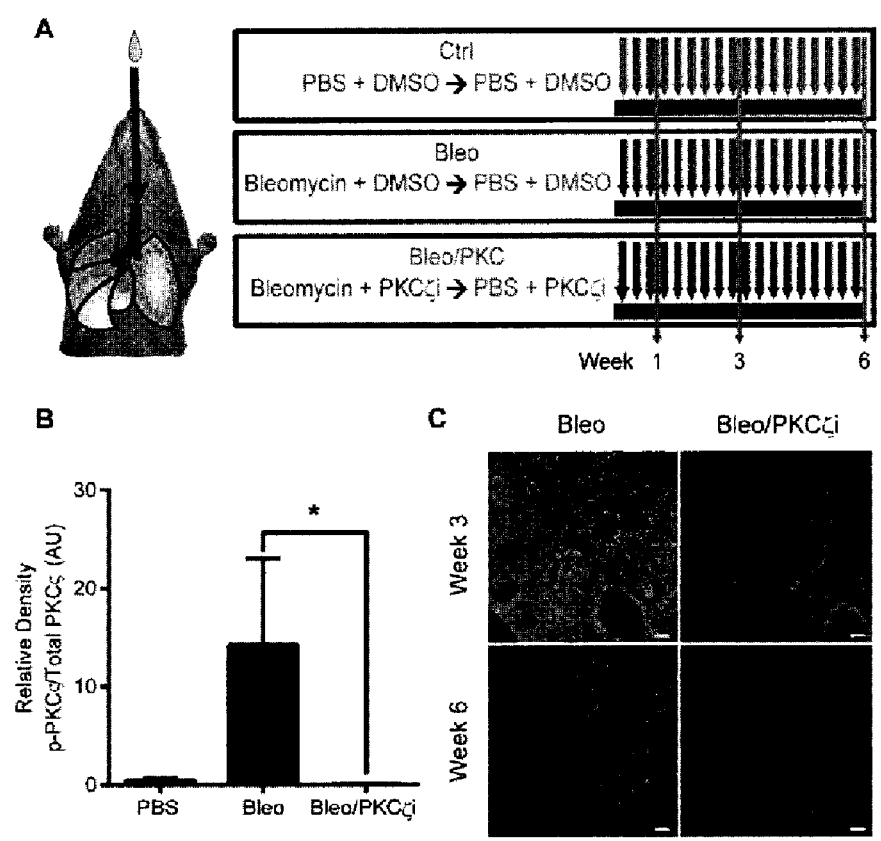
FIG. 1. PKCζi prevents activation of PKCζ in vivo. (A) Schematic of the bleomycin induced ALI model. Mice were randomly distributed into three groups: i) Control (Ctrl): received initial instillation of PBS+DMSO (blue arrow) followed by the same solution. ii) Bleomycin (Bleo)

Animal protocols were approved by the Institutional Animal Care and Use Committee at the University of Iowa. C57BL/6 mice (Jackson Laboratories, Bar Harbor, Me.) were anesthetized followed by intratracheal instillation of: (A) Control (Ctrl): 1 μl of DMSO (Sigma, St. Louis, Mo.) plus 49 μl of PBS; (B) Bleomycin (Bleo): 1 μl of DMSO plus 49 μl of bleomycin (APP pharmaceuticals, LLC Schaumburg, Ill.) dissolved in PBS (4 U/kg); (C) Bleomycin/PKCζi (Bleo/PKCζi): 1 μg of PKCζi (Calbiochem EMD Biosciences, San Diego, Calif.) solubilized in 1 μl of DMSO plus 49 μl of bleomycin (4 U/Kg) dissolved in PBS (Calbiochem EMD Biosciences, San Diego, Calif.). After this treatment, all mice were instilled (50 μl) every 72 hours with 1 μl of DMSO plus 49 μl of PBS in the Ctrl and Bleo group or with 1 μg of PKCζi dissolved in 1 μl of DMSO plus 49 μl of PBS in the Bleo/PKCζi group for the duration of the experiment. Mice were treated for up to 6 weeks (FIG. 1A). All conditions had between 4 to 6 animals.

Western-Blot Analysis

Western blot analysis was performed using Phospho-(Ser) PKCζ substrate rabbit monoclonal antibody (Cell Signaling, Beverly, Mass.), total PKCζ rabbit polyclonal antibody (Santa Cruz Biotechnology, Dallas, Tex.) and mature surfactant protein C (SPC) rabbit polyclonal antibody (Seven Hill Bioreagents, Cincinnati, Ohio).

Lung Histology

After dissection, immunofluorescence labeling was performed on frozen mouse lung tissue sections with polyclonal anti p-PKCζ (Santa Cruz Biotechnology, Dallas, Tex.) or monoclonal β4 antibody (Clone 346-11a, BD Biosciences, San Jose, Calif.) (23). In addition, Terminal deoxynucleotidyltransferase dUTP nick end labeling (TUNEL) staining was performed on week 1 mouse lung tissue sections (24).

Assay of Mouse BAL.

Bronchoalveolar lavage was performed as previously described (18). Total cell count was examined by hemocytometer and the percent of neutrophils cells in the bronchoalveolar lavage fluid (BALF) by cytospin slides stained with Wright's-Giemsa. Total protein concentration was measured by Bradford assay (Bio-Rad, Hercules, Calif.).

Measurement of ROS

BALF cells from week 1 post initial instillation were determined by the p-hydroxyphenylacetate method as reported previously (25).

Cytokine Measurements

Mouse IL-1β and active transforming growth factor beta (TGFβ) were measured using an ELISA from R&D Biosystems (Minneapolis, Minn.).

Lung Compliance

Mice were anesthetized, paralyzed and lung function assessed with the flexiVent Legacy. (SCIREQ Inc., Montreal, Canada).

Assessment of Collagen Deposition

The collagen content in the lung homogenates was determined with a hydroxyproline assay, as described previously (26). In addition, lung collagen deposition was examined in lung sections stained with Masson's trichrome.

Mouse Micro Computed Tomography (μCT) Scan

High resolution scanning coupled to a computer controlled respirator to reduce ventilation motion artifacts was performed as described previously (27).

Integrin β4$^+$ DLEP Cell Isolation

Integrin β4$^+$ cells were isolated using flow cytometry and were seeded in matrigel as previously described with modifications (23). Cells were grown for two weeks in the presence of PBS, DMSO (1:1000) or PKCζi (1:1000, 520 nM final concentration PKC). In order to recreate the microenvironment, the media was supplemented with 20% BALF from bleomycin treated mice from week 1 similar to previously described (4).

Statistical Analysis

Data is expressed as mean SEM. We used Kruskal-Wallis test with Dunn's multiple comparisons test in nonparametric distributions, while the unpaired Student's t-test was used in groups with normal distributions. Western blot densitometry signal was analyzed using Image Studio 5.x (LI-COR, Lincoln, Nebr.). Data analysis was performed using GraphPad Software 6.00, for Windows (GraphPad Software, La Jolla, Calif.).

Results

PKCζi Prevents PKCζ Activation in a Bleomycin ALI Mouse Model.

To determine whether PKCζ was activated in a bleomycin induced ALI mouse model, lungs were harvested and phosphorylation of PKCζ was determined at week 1, 3 and 6. Western blot was performed in lung homogenates of mice from week 1 against p-PKCζ and total PKCζ. Densitometry analysis evidenced increased ratio p-PKC/total PKCζ in the Bleo group. Conversely, the PKCζi group prevented bleomycin induced increased ratio p-PKC/total PKCζ (FIG. 1B). Immunoflurescence at week 3, showed uniform increase fluorescence for p-PKCζ (FIG. 1B), while mice treated with PKCζi did not have any increase in p-PKCζ at week 3. This uniform increase was not due to increase in secondary antibody unspecific binding. In addition, at week 3 and 6 the bleomycin only treated group seemed to turn off the activation of PKCζ, having a similar intensity when compared to mice treated with PKCζ (FIG. 1C).

Since bleomycin increases ROS production, and ROS are involved in PKCζ activation (17, 28), the effect of PKCζi on ROS production was tested. PKCζi does not reduce extracellular hydrogen peroxide ($H_2O_2$) in BALF isolated cells from bleomycin treated mice lung. This result suggests that the effect of PKCζi is ROS independent.

PKCζi does not Prevent Bleomycin Induced Lung Inflammation and Cell Death

PKCζ has been reported to regulate the inflammatory response of different organs (6-8). Accordingly, it was determined whether PKCζi treatment would prevent the development of lung inflammation in our ALI model. As shown in FIGS. 2A & B, PKCζi neither prevented the increase in BALF cell and neutrophil count, nor prevented the increase in IL-1β concentration. In addition, it was found that PKCζi did not prevent the increase in apoptotic cells by TUNEL+ staining. These results suggest that PKCζi does not interfere with the lung inflammatory response and apoptosis in the bleomycin model.

PKCζi Preserves Lung Compliance and Decreases Alveolar-Capillary Protein Permeability One of the clinical hallmarks of ALI is the decrease of lung compliance. As shown in FIG. 2C, the initial bleomycin instillation decreased lung compliance in the bleomycin and the Bleo/PKCζi group compare to control. However, Bleo/PKCζi group had a partial but statistically significant prevention in the lung compliance decrease compared to bleomycin alone group.

Lung compliance is negatively affected by the decrease in lung surfactant and the fluid leak from the damaged epithelial barrier. PKCζ has been reported to be involved in surfactant production (29). The total amount of SPC in whole lungs was examined by Western blot analysis. As shown in FIG. 2D, PKCζi did not prevent the reduction in SPC caused by bleomycin injury. Conversely, PKCζi prevented the increase in mice BALF protein concentration compared to bleomycin group (FIG. 2E).

Effect of PKCζi on Collagen Deposition

The fibroproliferative phase is part of the injury-repair process (30). To examine the effect of PKCζi on this phase, mouse lungs were harvested three weeks after bleomycin instillation. BALF active TGF β concentration, a critical mediator in ALI, and total lung hydroxyproline, a quantitative indicator of collagen deposition (31-34) were measured. As shown in FIGS. 3 A & B, PKCζi treated mice had no difference in active TGF β and hydroxyproline concentrations compared to bleomycin group. These data suggest that PKCζi does not prevent the fibroproliferation observed at week 3.

PKCζi Promotes Lung Repair In Vivo

It is recognized that repair mechanisms are essential in the resolution of ALI (2, 4, 35). Since it is shown in FIG. 3 that PKCζi did not alter the lung collagen deposition and TGFβ concentration at week 3, it was examined whether PKCζi treatment at week 6 would show evidence of lung injury resolution. As shown in FIG. 4 A-C, biochemical (active TGF β and total lung hydroxyproline) and histological evidence (Masson staining), demonstrated lung injury resolution in the PKCζi treated group while it persisted in the bleomycin group. Furthermore, lung μCT of PKCζi treated groups confirmed lung injury resolution (FIG. 6D).

When mice were treated with PKCζi only during the first week, they had increase hydroxyproline content similar to Bleomycin alone group at week 6. These results suggest that decreased alveolar-capillary permeability and improvement in lung compliance are not sufficient to observe early ALI resolution in this model. Therefore, it was proposed that continuous PKCζi treatment is needed to promote early lung repair.

PKCζi Promotes Proliferation of Distal Lung Epithelial Progenitor Cells In Vivo

Recently, Chapman and colleagues reported that integrin α6β4+ identifies a population of lung epithelial cells with regenerative potential in mice (4, 23). Li and colleagues reported this population of cells in human lungs (36). Therefore, the presence of these cells in mice treated with PKCζi at week 3 and 6 after bleomycin injury was examined by immunofluorescence. As shown in FIGS. 5A&B, there was an increase in DLEP integrin β4+ cells in the PKCζi treated mice at week 3. This became statistically significant at week 6. This result suggests that PKCζi increases the number of DLEP integrin β4+ cells in viva.

PKCζi Promotes Proliferation of DLEP Cells In Vitro

To test the hypothesis that PKCζ can promote proliferation of β4+ DLEP cells, integrin β4+ cells were isolated and the media was supplemented with BALF from bleomycin treated mice from week 1 in the presence of PBS, DMSO or PKCζ, in order to recreate the microenvironment in a similar approach as Vaughan and colleagues (4). The PKCζi treated group had increased number of large colonies compared to either DMSO or the PBS group. As shown in FIGS. 5 C & D, PKCζi increased proliferation of DLEP integrin β4+ cells in vitro compared to control.

Discussion

ALI is a major cause of respiratory failure and mortality in the intensive care unit. Except for lung protective ventilation strategies (37), pharmacological therapies for the treatment of ALI have failed to decrease mortality (38). Identifying the mechanisms involved in lung injury repair is critical for formulating novel targeted therapies.

The results demonstrate that PKCζi did not affect the neither the inflammatory response nor cell apoptosis. The exact mechanism of decreased protein permeability and improved lung compliance is yet to be elucidated. It is proposed that PKCζi preserves lung compliance after bleomycin injury by maintaining the integrity of the lung epithelial barrier via maintaining cell adhesions as described in other models of ALI (18, 19). However, PKCζi could play a role in other mechanisms such as early repair of the lung epithelial barrier by proliferation of fibroblasts (39) and/or early collagen deposition as described for other PKC isozymes (40).

ALI is a dynamic process in which there is a simultaneous activation of both inflammatory and fibrotic process (2, 41, 42). TGFβ is a critical mediator in ALI which is increased during the exudative and fibroproliferative phase (31, 43). The results demonstrate that PKCζ did not change collagen deposition or activation of TGFβ at week 3. These results suggest that mechanisms involved in the development of the fibroproliferative phase are not affected by PKCζi.

PKCζi promoted resolution of ALI as biochemical, histological and μCT imaging were similar to control animals. Current models of tissue regeneration attributes an important role in lung repair to club cells and alveolar type II cells (44, 45). However, there are progenitor cells residing at multiple airway locations, which have numerous clonal and differentiation potentials (46). Recently, Chapman and colleagues (23) reported that integrin β4+ identifies an adult DLEP cell population with regenerative potential in mice, which may help to maintain alveolar epithelial cells during lung repair. Furthermore, Li and colleagues reported that the same marker also identifies human DLEP cells with the potential to differentiate into Keratin 5 positive cells de novo (36). Keratin 5 positive cells have been shown to be involved in the process of alveolar regeneration in both bleomycin and influenza lung injury model (47, 48). Therefore, there is significant potential for therapies targeting these DLEP cells that could regenerate lung epithelial cells. The results suggest that mice treated with PKCζi had increase β4+DLEP at week 6. The results were recapitulated in vitro by a colony proliferation assay.

A possible mechanism of proliferation of DLEP β4+ cells is by inhibition of Notch signalling. Persistent Notch activation after injury (mouse and human) led to parenchymal "microhoneycombing", indicative of failed regeneration (4). When Notch is active, PKCζ can increase its activity by enhancing the production of Notch intracellular domain (49). Alternatively, PKCζ activates of the cellular master regulator of the antioxidant response Nuclear factor erythroid 2-related factor 2 (Nrf2) (50) and the latter has been implicated in the activation of the Notch pathway (51). Therefore, it is speculated that inhibition of PKCζ might promote DLEP cells proliferation by inhibiting Notch activation. Recent report of Vaughan and colleagues supported that in vivo inhibition of Notch signaling promoted a significant increase in SPC$^+$ cells derived from integrin β4$^+$ cells progenitor cells.

In summary, as shown in FIG. 6, this work proposes that PKCζi partially preserves lung compliance and decreases protein permeability after an injurious event. In addition, PKCζi promotes lung injury resolution and increases the proliferation of β4$^+$ DLEP cells, which may differentiate into alveolar epithelial cells contributing to the injury resolution. Thus, novel targeted therapies to inhibit PKCζ can be used to promote lung repair.

Example 2 References

1. Walkey A J, Summer R, Ho V, Alkana P. Acute respiratory distress syndrome: epidemiology and management approaches. *Clin Epidemiol* 2012; 4: 159-169.
2. Matthay M A, Ware L B, Zimmerman G A. The acute respiratory distress syndrome. *J Clin Invest* 2012; 122: 2731-2740.
3. Ware L B, Matthay M A. The acute respiratory distress syndrome. *The New England journal of medicine* 2000; 342: 1334-β49.
4. Vaughan A E, Chapman H A. Regenerative activity of the lung after epithelial injury. *Biochim Biophys Acta* 2013; 1832: 922-930.
5. Suzuki A, Ishiyama C, Hashiba K, Shimizu M, Ebnet K, Ohno S. aPKC kinase activity is required for the asymmetric differentiation of the premature junctional complex during epithelial cell polarization. *J Cell Sci* 2002; 115: 3565-3573.
6. Duran A, Diaz-Meco M T, Moscat J. Essential role of RelA Ser311 phosphorylation by zetaPKC in NF-kappaB transcriptional activation. *Embo J* 2003; 22: 3910-3918.
7. Duran A, Rodriguez A, Martin P, Serrano M, Flores J M, Leitges M, Diaz-Meco M T, Moscat J. Crosstalk between PKCzeta and the IL4/Stat6 pathway during T-cell-mediated hepatitis. *Embo J* 2004; 23: 4595-4605.
8. Yao H, Hwang J W, Moscat J, Diaz-Meco M T, Leitges M, Kishore N, Li X, Rahman I. Protein kinase C zeta mediates cigarette smoke/aldehyde- and lipopolysaccharide-induced lung inflammation and histone modifications. *The Journal of biological chemistry* 2010; 285: 5405-5416.
9. Chiba H, Osanai M, Murata M, Kojima T, Sawada N. Transmembrane proteins of tight junctions. *Biochim Biophys Acta* 2007.
10. Gonzalez-Mariscal L, Betanzos A, Nava P, Jaramillo B E. Tight junction proteins. *Prog Biophys Mol Biol* 2003; 81: 1-44.
11. Clarke H, Soler A P, Mullin J M. Protein kinase C activation leads to dephosphorylation of occludin and tight junction permeability increase in LLC-PK1 epithelial cell sheets. *J Cell Sci* 2000; 113 (Pt 18): 3187-3196.
12. Rajendran G, Dutta D, Hong J, Paul A, Saha B, Mahato B, Ray S, Home P, Ganguly A, Weiss M L, Paul S. Inhibition of protein kinase C signaling maintains rat embryonic stem cell pluripotency. *The Journal of biological chemistry* 2013; 288: 24351-24362.
13. Llado V, Nakanishi Y, Duran A, Reina-Campos M, Shelton P M, Linares J F, Yajima T, Campos A, Aza-Blanc P, Leitges M, Diaz-Meco M T, Moscat J. Repression of Intestinal Stem Cell Function and Tumorigenesis through Direct Phosphorylation of beta-Catenin and Yap by PKC-zeta. *Cell reports* 2015.
14. Mondrinos M J, Kennedy P A, Lyons M, Deutschman C S, Kilpatrick L E. Protein kinase C and acute respiratory distress syndrome. *Shock* 2013; 39: 467-479.
15. Breitkreutz D, Braiman-Wiksman L, Daum N, Denning M F, Tennenbaum T. Protein kinase C family: On the crossroads of cell signaling in skin and tumor epithelium. *J Cancer Res Clin Oncol* 2007; 133: 793-808.
16. Leitges M, Sanz L, Martin P, Duran A, Braun U, Garcia J F, Camacho F, Diaz-Meso M T, Rennert P D, Moscat J. Targeted disruption of the zetaPKC gene results in the impairment of the NF-kappaB pathway. *Mol Cell* 2001; 8: 771-780.
17. Konishi H, Tanaka M, Takemura Y, Matsuzaki H, Ono Y, Kikkawa U, Nishizuka Y. Activation of protein kinase C by tyrosine phosphorylation in response to H2O2. *Proc Natl Acad Sci USA* 1997; 94: 11233-11237.
18. Caraballo J C, Borcherding J, Thorne P S, Comellas A P. Protein kinase C-zeta mediates lung injury induced by diesel exhaust particles. *Am J Respir Cell Mol Biol* 2013; 48: 306-313.
19. Caraballo J C, Yshii C, Butti M L, Westphal W, Borcherding J A, Allamargot C, Comellas A P. Hypoxia increases transepithelial electrical conductance and reduces occludin at the plasma membrane in alveolar epithelial cells via PKC-zeta and PP2A pathway. *American journal of physiology Lung cellular and molecular physiology* 2011; 300: L569-578.
20. Eichholtz T, de Bont D B, de Widt J, Liskamp R M, Ploegh H L. A myristoylated pseudosubstrate peptide, a novel protein kinase C inhibitor. *The Journal of biological chemistry* 1993; 268: 1982-1986.
21. Matute-Bello G, Frevert C W, Martin T R. Animal models of acute lung injury. *American journal of physiology Lung cellular and molecular physiology* 2008; 295: L379-399.
22. Mouratis M A, Aidinis V. Modeling pulmonary fibrosis with bleomycin. *Current opinion in pulmonary medicine* 2011; 17: 355-361.
23. Chapman H A, Li X, Alexander J P, Brumwell A, Lorizio W, Tan K, Sonnenberg A, Wei Y, Vu T H. Integrin alpha6beta4 identifies an adult distal lung epithelial population with regenerative potential in mice. *J Clin Invest* 2011; 121: 2855-2862.
24. Lawson W E, Polosukhin V V, Stathopoulos G T, Zoia O, Han W, Lane K B, Li B, Donnelly E F, Holburn G E, Lewis K G, Collins R D, Hull W M, Glasser S W, Whitsett J A, Blackwell T S. Increased and prolonged pulmonary fibrosis in surfactant protein C-deficient mice following intratracheal bleomycin. *The American journal of pathology* 2005; 167: 1267-1277.
25. He C, Murthy S, McCormick M L, Spitz D R, Ryan A J, Carter A B. Mitochondrial Cu,Zn-superoxide dismutase mediates pulmonary fibrosis by augmenting H2O2 generation. *The Journal of biological chemistry* 2011; 286: 15597-15607.
26. Englert J M, Hanford L E, Kaminski N, Tobolewski J M, Tan R J, Fattman C L, Ramsgaard L, Richards T J, Loutaev I, Nawroth P P, Kasper M, Bierhaus A, Oury T D. A role for the receptor for advanced glycation end products in idiopathic pulmonary fibrosis. *The American journal of pathology* 2008; 172: 583-591.

27. Namati E, Chon D, Thiesse J, Hoffman E A, de Ryk J, Ross A, McLennan G. In vivo micro-CT lung imaging via a computer-controlled intermittent iso-pressure breath hold (IIBH) technique. *Physics in medicine and biology* 2006; 51: 6061-6075.
28. Wallach-Dayan S B, Izbicki G, Cohen P Y, Gerstl-Golan R, Fine A, Breuer R. Bleomycin initiates apoptosis of lung epithelial cells by ROS but not by Fas/FasL pathway. *American journal of physiology Lung cellular and molecular physiology* 2006; 290: L790-L796.
29. Gobran L I, Xu Z X, Rooney S A. PKCζ isoforms and other signaling proteins involved in surfactant secretion in developing rat type II cells. *Am J Physiol* 1998; 274: L901-907.
30. Burnham E L, Hyzy R C, Paine R, 3rd, Kelly A M, Quint L E, Lynch D, Curran-Everett D, Moss M, Standiford T J. Detection of Fibroproliferation by Chest High Resolution Computed Tomography in Resolving Acute Respiratory Distress Syndrome. *Chest* 2014.
31. Pittet J F, Griffiths M J, Geiser T, Kaminski N, Dalton S L, Huang X, Brown L A, Gotwals P J, Koteliansky V E, Matthay M A, Sheppard D. TGF-beta is a critical mediator of acute lung injury. *J. Clin Invest* 2001; 107: 1537-1544.
32. Khalil N, Parekh T V, O'Connor R, Antman N, Kepron W, Yehaulaeshet T, Xu Y D, Gold L I. Regulation of the effects of TGF-beta 1 by activation of latent TGF-beta 1 and differential expression of TGF-beta receptors (T beta R-I and T beta R-II) in idiopathic pulmonary fibrosis. *Thorax* 2001; 56: 907-915.
33. Khalil N, O'Connor R N, Flanders K C, Unruh H. TGF-beta 1, but not TGF-beta 2 or TGF-beta 3, is differentially present in epithelial cells of advanced pulmonary fibrosis: an Immunohistochemical study. *Am J Respir Cell Mol Biol* 1996; 14: 131-138.
34. Pickrell J A, Shafer J. Lung connective tissue measurements. I. Amino acid analysis procedures for determination of canine lung connective tissue. *Archives of internal medicine* 1971; 127: 891-895.
35. Hogan B L, Barkauskas C E, Chapman H A, Epstein J A, Jain R, Hsia C C, Niklason L, Calle E, Le A, Randell S H, Rock J, Snitow M, Krummel M, Stripp B R, Vu T, White E S, Whitsett J A, Morrisey E E. Repair and Regeneration of the Respiratory System: Complexity, Plasticity, and Mechanisms of Lung Stem Cell Function. *Cell stem cell* 2014; 15: 123-138.
36. Li X, Rossen N, Sinn P L, Hornick A L, Steines B R, Karp P H, Ernst S E, Adam R J, Moninger T O, Levasseur D N, Zabner J. Integrin alpha6beta4 identifies human distal lung epithelial progenitor cells with potential as a cell-based therapy for cystic fibrosis lung disease. *PloS one* 2013; 8: e83624.
37. Brower R M G, Morris M A, Schoenfeld A, Thompson D, Wheeler B T, Wiedemann A, Arroliga H P, FIsher A C et al. Ventilation with lower tidal volumes as compared with traditional tidal volumes for acute lung injury and the acute respiratory distress syndrome. The Acute Respiratory Distress Syndrome Network. *The New England journal of medicine* 2000; 342: 1301-1308.
38. Levitt J E, Matthay M A. Treatment of acute lung injury: historical perspective and potential future therapies. *Seminars in respiratory and critical care medicine* 2006; 27: 426-437.
39. Short M D, Fox S M, Lam C F, Stenmark K R, Das M. Protein kinase Czeta attenuates hypoxia-induced proliferation of fibroblasts by regulating MAP kinase phosphatase-1 expression. *Molecular biology of the cell* 2006; 17: 1995-2008.
40. Luzina I G, Highsmith K, Pochetuhen K, Nacu N, Rao J N, Atamas S P. PKCalpha mediates CCL18-stimulated collagen production in pulmonary fibroblasts. *Am J Respir Cell Mol Biol* 2006; 35: 298-305.
41. Budinger G R, Chandel N S, Donnelly H K, Eisenbart J, Oberoi M, Jain M. Active transforming growth factor-beta1 activates the procollagen I promoter in patients with acute lung injury. *Intensive care medicine* 2005; 31: 121-128.
42. Chesnutt A N, Matthay M A, Tibayan F A, Clark J G. Early detection of type III procollagen peptide in acute lung injury. Pathogenetic and prognostic significance. *American journal of respiratory and critical care medicine* 1997; 156: 840-845.
43. Fahy R J, Lichtenberger F, McKeegan C B, Nuovo G J, Marsh C B, Wewers M D. The acute respiratory distress syndrome: a role for transforming growth factor-beta 1. *Am J Respir Cell Mol Biol* 2003; 28: 499-503.
44. Barkauskas C E, Cronce M J, Rackley C R, Bowie E J, Keene D R, Stripp B R, Randell S H, Noble P W, Hogan B L. Type 2 alveolar cells are stem cells in adult lung. *J Clin Invest* 2013; 123: 3025-3036.
45. Kotton D N, Morrisey E E. Lung regeneration: mechanisms, applications and emerging stem cell populations. *Nature medicine* 2014; 20: 822-832.
46. Chen H, Matsumoto K, Brockway B L, Rackley C R, Liang J, Lee J H, Jiang D, Noble P W, Randell S H, Kim C F, Stripp B R. Airway epithelial progenitors are region specific and show differential responses to bleomycin-induced lung injury. *Stem cells* 2012; 30: 1948-1960.
47. Zheng D, Yin L, Chen J. Evidence for Scgb1a1(+) cells in the generation of p63(+) cells in the damaged lung parenchyma. *Am J Respir Cell Mol Biol* 2014; 50: 595-604.
48. Zuo W, Zheng T, Wu D Z, Guan S P, Liew A A, Yamamoto Y, Wang X, Lim S J, Vincent M, Lessard M, Crum C P, Xian W, McKeon F. p63Krt5 distal airway stem cells are essential for lung regeneration. *Nature* 2014.
49. Sjoqvist M, Antfolk D, Ferraris S, Rraklli V, Haga C, Antila C, Mutvei A, Imanishi S Y, Holmberg J, Jin S, Eriksson J E, Lendahl U, Sahlgren C. PKCzeta regulates Notch receptor routing and activity in a Notch signaling-dependent manner. *Cell research* 2014; 24: 433-450.
50. Gjyshi O, Flaherty S, Veettil M V, Johnson K E, Chandran B, Bottero V. Kaposi's sarcoma-associated herpesvirus induces Nrf2 activation in latently infected endothelial cells through SQSTM1 phosphorylation and interaction with polyubiquitinated Keap1. *Journal of virology* 2015; 89: 2268-2286.
51. Paul M K, Bisht B, Darmawan D O, Chiou R, Ha V L, Wallace W D, Chon. A T, Hegab A E, Grogan T, Elashoff D A, Alva-Omelas J A, Gomperts B N. Dynamic changes in intracellular ROS levels regulate airway basal stem cell homeostasis through Nrf2-dependent Notch signaling. *Cell stem cell* 2014; 15: 199-214.

Example 3

PKCζi Promotes Proliferation of α6β4⁺ Cells In Vitro

Isolated mouse DLEP α6β4⁺ cells in the presence of 20% of BALF from week 1 mice injured with bleomycin were treated with PKCζi (10 μM) for 2 weeks. At week 3 the colonies derived from cre-GFP (lox-tm-TR/GFP) for surfactant protein C (SPC)/Tomato red with hydroxy-tamoxifen were exposed in order to trace the differentiation of β4⁺ colonies into SPC+ cells. As shown in FIG. 7, these colonies can differentiate into SPC+ cells. PKCζi increased the number of α6β4+ colonies compared to control. These results support the hypothesis the PKCζi increase α6β4+ DLEP cells with regenerative potential in vitro and in vivo.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Tyr Arg Arg Gly Ala Arg Arg Trp Arg Lys Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl

<400> SEQUENCE: 2

Ser Ile Tyr Arg Arg Gly Ala Arg Arg Trp Arg Lys Leu
1               5                   10
```

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying

What is claimed is:

1. A therapeutic method for treating Acute Respiratory Distress Syndrome or Acute Lung Injury in a mammal, wherein lung cell injury is implicated and lung progenitor cell proliferation is desired, comprising administering to a mammal in need of such therapy, an effective amount of a composition comprising the peptide of SEQ ID NO:2

N-Myristoyl-Ser-Ile-Tyr-Arg-Arg-Gly-Ala-Arg-Arg-Trp-Arg-Lys-Leu-OH and a physiologically acceptable carrier, wherein the peptide is administered orally, by inhalation, by bronchoscopic instillation, or by intra-airway aerosol.

2. The method of claim 1, wherein the peptide is administered multiple times.

3. The method of claim 2, wherein the peptide is administered at an interval of 24 hours, 48 hours, 72 hours, or once per week.

4. A method to treat Acute Respiratory Distress Syndrome or Acute Lung Injury or to induce proliferation of lung progenitor cells comprising administering a therapeutically effective amount of a composition comprising the peptide of SEQ ID NO:2

N-Myristoyl-Ser-Ile-Tyr-Arg-Arg-Gly-Ala-Arg-Arg-Trp-Arg-Lys-Leu-OH and a physiologically acceptable carrier to a mammal in need thereof, wherein the peptide is administered orally, by inhalation, by bronchoscopic instillation, or by intra-airway aerosol.

5. The method of claim 4, wherein the peptide is administered multiple times.

6. The method of claim 5, wherein the peptide is administered at an interval of 24 hours, 48 hours, 72 hours, or once per week.

* * * * *

UNITED STATES PATENT AND TRADEMARK OFFICE
CERTIFICATE OF CORRECTION

PATENT NO. : 10,328,114 B2  
APPLICATION NO. : 14/925826  
DATED : June 25, 2019  
INVENTOR(S) : Alejandro P. Comellas Freymond et al.

Page 1 of 1

It is certified that error appears in the above-identified patent and that said Letters Patent is hereby corrected as shown below:

On the Title Page

Item (60), Related U.S. Application Data, please delete "Provisional application No. 62/069,694, filed on Oct. 28, 2015" and insert -- Provisional application No. 62/069,694, filed on Oct. 28, 2014 -- therefor.

Signed and Sealed this  
First Day of October, 2019

Andrei Iancu  
*Director of the United States Patent and Trademark Office*